US010073074B1

(12) United States Patent
Kumar et al.

(10) Patent No.: US 10,073,074 B1
(45) Date of Patent: Sep. 11, 2018

(54) LOW RF-BAND IMPEDANCE SPECTROSCOPY BASED SENSOR FOR IN-SITU, WIRELESS SOIL SENSING

(71) Applicant: IOWA STATE UNIVERSITY RESEARCH FOUNDATION, INC., Ames, IA (US)

(72) Inventors: Ratnesh Kumar, Ames, IA (US); Robert J. Weber, Boone, IA (US); Gunjan Pandey, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 497 days.

(21) Appl. No.: 14/695,763

(22) Filed: Apr. 24, 2015

Related U.S. Application Data

(60) Provisional application No. 61/984,531, filed on Apr. 25, 2014.

(51) Int. Cl.
*G01R 27/08* (2006.01)
*G01N 33/24* (2006.01)
*G01N 27/02* (2006.01)

(52) U.S. Cl.
CPC ......... *G01N 33/246* (2013.01); *G01N 27/028* (2013.01); *G01N 2033/245* (2013.01)

(58) Field of Classification Search
CPC .................... G01N 33/246; G01N 27/028
See application file for complete search history.

(56) References Cited

U.S. PATENT DOCUMENTS

| 5,033,397 | A | 7/1991 | Colburn, Jr. |
| 5,193,217 | A * | 3/1993 | Lunn .................. H04B 1/46 455/79 |
| 5,434,511 | A * | 7/1995 | Adamian ............. G01R 35/005 324/601 |
| 5,673,637 | A | 10/1997 | Colburn, Jr. et al. |
| 6,138,590 | A | 10/2000 | Colburn, Jr. |
| 6,484,652 | B1 | 11/2002 | Colburn, Jr. |
| 7,339,957 | B2 | 3/2008 | Hitt |
| 8,354,852 | B1 | 1/2013 | Campbell et al. |
| 8,444,937 | B2 | 5/2013 | Tuli et al. |
| 2003/0117321 | A1* | 6/2003 | Furse .................. H01Q 1/36 343/700 MS |

(Continued)

FOREIGN PATENT DOCUMENTS

WO    2008116244    10/2008

OTHER PUBLICATIONS

Huang et al., Development of a Wireless Soil Sensor Network, 2008 ASABE Annual International Meeting, 2008.*

(Continued)

*Primary Examiner* — Daniel Miller
(74) *Attorney, Agent, or Firm* — McKee, Voorhees & Sease, PLC

(57) ABSTRACT

A soil sensor includes a housing, an antenna disposed within the housing, a measurement circuit disposed within the housing and operatively connected to the antenna, the circuit configured to measure impedance of soil at a plurality of different frequencies using the antenna as a sensor electrode, and a wireless interface disposed within the housing and operatively connected to the antenna and configured for wireless communications over the antenna at its communications frequency.

18 Claims, 14 Drawing Sheets

(56) References Cited

U.S. PATENT DOCUMENTS

| | | |
|---|---|---|
| 2006/0035618 A1* | 2/2006 | Pleasant .............. H04B 1/0096 455/323 |
| 2006/0178847 A1 | 8/2006 | Glancy et al. |
| 2010/0112614 A1 | 5/2010 | Axelrod et al. |
| 2011/0115499 A1 | 5/2011 | Chodavarapu et al. |
| 2013/0248212 A1 | 9/2013 | Bassett |
| 2013/0250305 A1 | 9/2013 | Holland |

OTHER PUBLICATIONS

K. Barkeshli, A C-Band Microwave Dielectric Probe for In-Situ Detection of Soil Moisture, Department of Electrical Engineering and Computer Science, Univeristy of Michigan, 1985.*

Agilent, Basics of Measuring the Dielectric, Properties of Materials, 2006, pp. 15, 17.*

Skierucha et al., A FDR Sensor for Measuring Complex Soil Dielectric Permittivity in the 10-500 MHz Frequency Range, Sensors Oct. 2010, 3314-3329, 2010.*

Huang et al, Development of a Wireless Soil Sensor Network, 2008 ASABE Annual International Meeting, Providence, Rhode Island, Jun. 29-Jul. 2, 2008.*

Metamaterial antenna, available on Jan. 9, 2013 at https://en.wikipedia.org/wiki/Metamaterial_antenna.*

Soontornpipit et al., Optimization of a Buried Microstrip Antenna for Simultaneous Communication and Sensing of Soil Moisture, IEEE Transactions on Antennas and Propagation, vol. 54, No. 3, Mar. 2006.*

A. Tetyuev et al., Soil Type Characterization for Moisture Measurement by Impedance Spectroscopy, IMTC 2006—Instrumentation and Measurement Technology Conference, Sorrento, Italy, Apr. 2006.*

Pandey, et al., "Design and Implementation of a self-calibrating, compact micro strip sensor for in-situ dielectric spectroscopy and data transmission", IEEE Sensors Corp., 4 pages. Oct. 2013.

KR20020021704, SK Energy—English. Mar. 22, 2002.

KR20020040108, SK Energy—English. May 30, 2002.

KR20020040109, SK Energy—English. May 30, 2002.

WO2008116244, Austrian Research Centers Arc—English. Oct. 2, 2008.

* cited by examiner

LOW RF-BAND IMPEDANCE SPECTROSCOPY BASED SENSOR FOR IN-SITU, WIRELESS SOIL SENSING

CROSS-REFERENCE TO RELATED APPLICATIONS

This application claims priority under 35 U.S.C. § 119 to provisional application Ser. No. 61/984,531 filed Apr. 25, 2014, herein incorporated by reference in its entirety.

GRANT REFERENCE

This invention was made with government support under Grant Nos. CCF1331390 and ECCS0926029 awarded by National Science Foundation. The government has certain rights in the invention.

FIELD OF THE INVENTION

The present invention relates to sensing. More particularly, but not exclusively, the present invention relates to a low RF-band impedance spectroscopy based sensor suitable for use for in-situ, wireless soil sensing.

BACKGROUND OF THE INVENTION

Efficient management of agricultural resources for increased productivity and minimum environmental impact forms the basis of precision agriculture. In a generic precision agriculture layout, intra- and inter-field variabilities are characterized using a network of sensor nodes spread over a large area. Each sensor node sends local information about the properties of the soil surrounding it. All the information collected is sent to a central node which processes the information and takes necessary measures like irrigation and fertilization. Thus, each node in this sensor network not only measures the soil content accurately in real time, it also communicates efficiently with other nodes in the network in order to transmit the collected information. Although various sensors have been proposed, what is needed is an improved sensor that addresses numerous problems associated with in situ sensing.

SUMMARY OF THE INVENTION

An on-board solution is provided for a sensor which can measure local soil conditions like moisture as well as ion content with high accuracy. It also has the capability to sweep through a low radio frequency band-which extends from a few hundred KHz range up to a few hundred MHz-so as improve the data reliability of moisture and ionic content measurements. To achieve high accuracy and robustness of measurements, the sensor has a built-in self-calibrating system which is based on embedded measurements of open, short and matched load conditions. For efficient transmission, a built-in multi-power mode is introduced in transmission and reception. Such system has been shown to support more energy-efficient medium-access-control (MAC) protocol as introduced in [13].

Various features of such a system may include:
1. The soil properties (moisture, ionic concentrations) affect its dielectric behavior, and hence the measured impedance. The sensor has the capability to measure impedance at multiple frequencies. This improves accuracy and also gives the sensor the ability to detect ionic concentration [4].
2. The sensor has a built-in self-calibration system which makes it impervious to the variations in soil temperature and climatic conditions like hail, drought, rain etc.
3. The sensor is designed for in-situ underground operation through an in-built antenna and wireless transceiver, so as not to interfere with the above ground operations. To economize on size, the sensor probe is diplexed to act as antenna.
4. The built-in transceiver has multiple power modes for transmitter/receiver to support a highly energy efficient MAC (Medium Access Control) [13].

The sensor has a low power 'sleep' mode. In one embodiment, the sensor consumes only a few hundreds of microwatts of power compared to few watts of power in measurement mode Of course other embodiments are contemplated but preferably there are at least two modes of operation and the power consumption is markedly different between the different modes. When the sensor is not making measurements, it switches to sleep mode and waits for an external trigger to wake it up again. Power saved in this fashion increases the battery life of the sensor.

6. The sensor has a metamaterial-inspired small antenna that may be buried underground, and can transmit information using the antenna and may also act as sensing electrode in a frequency range that does not contain the transmission frequency. It is to be understood that the sensor may be used at any number of different frequencies for transmissions and may have any number of sensing ranges as may be appropriate in a particular application or embodiment.

Spectral impedance/dielectric sensing also has the potential to detect pathogens and undesired microbial growth whose presence changes the electric properties of the sample. Such spectroscopic dielectric sensing has been shown to be useful in detecting the presence of bacteria such as *E-coli* [15] after incubation with appropriate anti-microbial peptides (AMP). Microcapacitive sensors based on similar principle have shown direct proportionality between impedance changes due to change in the dielectric properties and the extent of analyte binding occurring on the surface of an electrode [5].

Many attempts have been made to accurately measure varying moisture levels in the soil. Notable approaches found in literature for soil-moisture measurement include thermal sensors [28], neutron probe sensors [24], granular matrix/gypsum block sensors [9], TDR/FDR based impedance measuring electronic sensors [7], [27], [17], [21]. Some of them are discussed here.

Thermal sensors determine the properties of the soil using the thermal properties like conduction and radiation. They are based on the principle that soil thermal properties vary with change in the moisture level and hence a measure of moisture content can be obtained by observing the change in these properties. Thermal Sensors discussed in [28] determine moisture content using these two methods (heat conduction and heat radiation). The heat conduction method uses a heater and temperature sensor separated by a distance and the temperature change in the soil is measured to determine the amount of moisture present. Heat radiation method uses a heater and two thermocouples-one of which is attached to the radiation plate connected to the heater and a second is placed on a patch attached to an aluminum plate kept at a distance from the heater. The temperature curves of thermocouples are then observed to see the thermal characteristic of the medium. Another thermal pulse sensor discussed in [23] generates a heat pulse whose durations and magnitude is controlled by a microprocessor. This heat pulse changes the voltage across the thermistor. The change in voltage across the thermistor is related to the moisture content by using the empirical relations provided in [22]. One inherent disadvantage of using a thermal sensor is that the installed heater can affect the moisture concentration around the sensor node causing evaporation and hence an accurate measure of soil content may not be determined. Also, due to the agricultural activities carried out in the soil, the thermal properties might change due to factors other than moisture. Some examples can be addition of fertilizers and loosening of soil due to ploughing. Hence a periodic calibration is needed.

Another approach used to measure soil moisture is to use a satellite system which can remotely measure the moisture content by GNSS-R (Global navigation satellite system reflection) signal [12]. Each sensor node has two antennae one of which points to the ground and the other to the satellite. The sensor measures the reflectivity of the soil, which primarily depends on the moisture content. This information is sent to the satellite and global data can be collected through a series of such sensor nodes. Since the nodes are placed above the ground and the depth to which a wave can travel is limited by the losses in the soil, this method does not necessarily provide actual moisture level which is available to the roots of the crops. Satellite based sensors can provide good accuracy, but spatial resolution is limited. Another GPR (ground penetration radar) based method is discussed in [3]. Using the Debye model for relaxation time of water molecules it is argued that the amount of water will affect the scattering characteristics of the signal reflected from the ground. Hence, the frequency spectrum of the received signal will give an indication of the water content present in the soil. A granular matrix based approach to the soil moisture sensing has been described in [9]. The sensor operates on the electrical resistance principle and is made of porous ceramic material as an external shell. Two electrodes are inserted in the internal matrix. As water content in the soil varies, the amount of water seeping in through the porous shell also changes. This changes the electrical resistance between two electrodes which can be monitored. Sensor contains a wafer of gypsum to protect the electrodes against salinity in the soil. An NIR (Near Infra-Red) spectrometer [1] is another type of sensor. The spectrophotometer is attached to the back of the subsoiler chisel to perform light reflectance measurement from the soil surface. The calibration is done under laboratory condition. This method is highly expensive due to sophisticated components involved. Also the measurement is done only while using the chisel which may not be required at all times.

A neutron probe sensor has been discussed in [24]. The authors provide computer modeling and testing for the neutron sensor which will work for top 15 cm of soil. In a neutron probe sensor, fast neutrons are emitted from a decaying source into the soil where they bounce around and gradually slowdown in the process mainly due to collisions with the hydrogen nuclei in the surroundings. Thermal and epithermal probes detect a fraction of these moderated neutrons depending on the concentration of hydrogen nuclei in the surroundings. In most soils, the only source of hydrogen would be water which means that the slowing down of fast neutrons would be due to water. These sensors, although very accurate, are more suited for reactor sites where radioactivity is not a problem. These are expensive due to cost of neutron probe and detector.

Impedance Sensors are a common type of sensor which have the potential to get rid of most of the inherent disadvantages (cost, sensitivity, resolution, in-situ real-time operability, etc.) which are present in thermal, granular matrix, neutron probes and remote no-contact sensors. Some of the advantages offered by impedance sensors are their ability to make measurements in real time, ease of sensor calibration, no effect of sensor on surrounding soil properties, no interference of sensor in agricultural processes, accuracy and ease of measurement. Moreover, impedance sensors can naturally form a part of a circuit which can include a transceiver and hence they can easily be embedded into a network. This further means that they are controllable from a remote station. These sensors can be calibrated to work for different types of soil and they work for large range of moisture content. The downside of impedance sensors is that all electrical circuits come with a certain amount of noise which affects accuracy. Many different types of impedance sensors are present in the literature. Fringing electric fields have been used in [16] to determine the permittivity of soil under observation. The experimental setup discussed uses a fringing capacitance followed by the FEM (finite element method) analysis to relate capacitance with permittivity. Variations in moisture content changes the permittivity which in turn changes the capacitance that can be detected. The setup lacks a self-calibration algorithm and requires measuring capacitance and permittivity for known moisture content from time to time. This is not practical especially for a large network of buried autonomous sensor nodes. The study has not been extended to analyzing nutrients besides moisture.

Another frequency domain approach has been suggested in [21]. Like in [16], a fringing field capacitance is used to project the sensing electric field into the surrounding material. An AC (Alternating Current) signal applied to this capacitor will shift its phase depending on equivalent RC model of capacitance. The phase shift has been shown to be proportional to $\sin^{-1}$ of the capacitance value. The driving signals follows two paths, one direct and another through soil container- to the phase detector. It is assumed that the only phase shift will occur in the soil containing capacitor which is a fair assumption given proper fabrication is done. Thus phase shift can be used to find capacitance which in turn can be used to determine dielectric constant of soil contained in the capacitive cell. Since, different frequencies will result in different phase change across the capacitor, calibration is needed every time the frequency is changed. Hence a multi-frequency implementation of this work becomes more complicated. FDR approach has also been used in [10] to develop an ASIC to measure the capacitance which has been mapped to permittivity and soil moisture. The sensor shows good accuracy and permittivity resolution.

Time Domain Reflectometry (TDR) has inspired many past and ongoing sensor designs. The basic idea is to direct a square pulse towards a soil sample and calculate the coefficient of reflection at the surface from which the wave gets reflected. The reflection coefficient along with the characteristic impedance of the line gives the impedance of the surface at which reflection takes place. Creation of the dielectric profile for the soil using TDR has been discussed in [27]. For the measurement of spatially resolved dielectric profiles by using delay time measurements, a transmission line is used. The delay time of an electromagnetic pulse along the transmission line is measured with the help of an industrial TDR system operating in the baseband up to 3 GHz with a pulse width of 300 ps. A phase-shift based approach for finding unknown impedance using TDR has been discussed in [8]. Phase shift in traveling wave along the length of transmission is proportional to the square root of permittivity. Thus knowing the phase shift gives the value of permittivity of the medium. In situ application of this method requires a high cost of TDR system. TDR method has additional drawbacks such as problems with extracting accurate parameters from the received waveforms, difficulties in detecting the reflected signal in saline soils, and dependence of measurement on the coaxial cable and probe lengths [3]. As used in this application, saline means a salt solution formed with different plant nutrients under consideration, not just sodium chloride solutions as is often meant.

To summarize, there is a definitive need for a sensor system which gives accurate results at multiple frequencies in real-time, is self-calibrating, can be operated in-situ yet be part of a network, consumes small amount of power and is relatively less expensive. Our approach involves reflection as in TDR systems, but instead of measuring the time delay or phase shift we measure the amplitude and phase of incident and reflected waves. This is beneficial for real time sensing as the sensing surface can be outside of the system unlike [21] which needs waves to travel through the conductor contained in the line. Our system has the capability to make measurements at multiple frequencies and is self-calibrating which makes it more robust, more accurate and low maintenance. Like capacitive measurement schemes used in [16] and [21], our system measures unknown impedance. Its measurements are based on reflectometry allowing us to make a direct correlation between impedance and permittivity. The use of transmission line model allows us to include line losses and calibrate the system periodically. Due to multi-frequency approach, our sensor has the capability to detect and transmit information about soil moisture as well as ionic concentration [4]. Using de-embedding techniques, some of the disadvantages related to TDR sensors like inaccurate measurements due to probe dimensions and other parasitic parameters have been removed.

The on-board solution for a robust, accurate and self-calibrating soil moisture and nutrient sensor with inbuilt wireless transmission and reception capability is provided as a part of the present invention. The sensor can make real time and accurate measurement of subsurface soil moisture and nutrients and is ideally suited to act as a node in a network spread over a large area. It works on the principle of impedance spectroscopy. Impedance measurement at multiple frequencies is done by comparing the amplitude and phase of signals incident on and reflected from the soil in proximity of the sensor. A distributed transmission line model for the on-board connections is employed to improve the accuracy of measurements. Variations in temperature and surroundings are accounted by realizing a built-in self-calibrating mechanism which operates on the standard short-open-load (SOL) technique. This also accounts for the parasitic impedance of the board in the measurements to minimize the errors. Measurements of both real and imaginary parts of soil impedance at multiple frequencies gives the sensor an ability to detect variations in ionic concentrations other than soil moisture content. A switch controlled multiple power mode transmission and reception is provided to support highly energy efficient medium access control as introduced in [13]. The invention presented here is based on publications [32], [33], [37], [38], [39], [40], [41]. All of which are incorporated by reference in their entireties.

A key challenge to underground, in-situ soil sensing with wireless interface is the antenna size. Smaller operating frequency supports lower path losses but increases the wavelength and hence the size of standard monopole (17 cm in height at 433 MHz) or rectangular microstrip patch antenna (24 cm×20 cm at 433 MHz), which is prohibitive for underground sensors. To circumvent the size problem, a composite right-left handed (CRLH) microstrip patch antenna for wireless transmission at 433 MHz that doubles up as an underground, sensing element (external capacitor) has been designed and fabricated, The combined antenna/sensing CRLH patch integrates with the previously implemented onboard, multi-frequency dielectric based impedance sensor for soil moisture and ion concentration determination and provides almost 93% reduction over the standard microstrip antenna size. The input impedance of the CRLH sensor, surrounded by the soil containing moisture and ions, is measured at multiple frequencies in the lab setting. It is shown that the change in moisture and ionic concentration can be successfully detected using the sensor. The small profile of the proposed antenna (3 cm×2 cm), that is almost 93% smaller, makes it ideal for compact packaging.

Therefore, it is a primary object, feature or advantage to improve over the state of the art.

It is a further object, feature, or advantage to provide a sensor suitable for measuring impedance characteristics of soil or other mediums at multiple frequencies in the sensing range which includes frequencies in low-radio frequency band (within few hundreds of MHz).

A still further object, feature, or advantage of the present invention is to provide a sensor which may use the same antenna structure as both an electrode for sensing and as an antenna for wireless communications.

Another object, feature, or advantage of the present invention is to provide a sensor which uses impedance spectroscopy.

Yet another object, feature, or advantage of the present invention is a sensor which is self-calibrating.

A still further object, feature, or advantage of the present invention is a sensor which is small in size.

Yet another object, feature, or advantage of the present invention is a sensor which can be used in sensing moisture and ionic concentrations.

A further object, feature, or advantage of the present invention is a sensor which is self-contained and has low power requirements.

A further object feature or advantage of the present invention is a low power or 'sleep' mode in which sensor consumes few hundred microwatts of power compared to a few watts of power consumption under measurement mode.

One or more of these and/or other objects, features, or advantages of the present invention will become apparent from the specification and claims that follow. No single embodiment need exhibit each and every object, feature, or advantage as different embodiments may have different objects, or advantages.

According to one aspect, a soil sensor includes a housing, an antenna disposed on the top surface of the housing exposed to the soil, a measurement circuit disposed within the housing and operatively connected to the antenna, the circuit configured to measure impedance of soil at a plurality of different frequencies using the antenna as a sensor electrode, and a wireless interface disposed within the housing and operatively connected to the antenna and configured for wireless communications over the antenna at one or more communications frequencies. The soil sensor may further include a diplexer operatively connected to the antenna. The antenna may be a metamaterial inspired structure. The soil sensor may further include a power source operatively connected to the measurement circuit and the wireless interface, the power source disposed within the housing. The measurement circuit may be configured for self-calibration using a known impedance. The measurement circuit may be configured for collecting data for determining soil moisture and the wireless interface provides for communicating the data wirelessly. The measurement circuit may be configured for collecting data for determining electrical conductivity associated with the soil and the wireless interface provides for communicating the data wirelessly. The circuit may be configured for collecting data for determining ion concentrations associated with the soil and the wireless interface provides for communicating the data wirelessly. The plurality of different frequencies may be in the range of 200 or 300 KHz (or less) to 400 or 500 MHz (or more). The one or more communication frequencies may be above sensing frequency and in a few hundred MHz range.

According to another aspect, a sensor includes a housing, an antenna disposed on the outside of one of the faces of the housing exposed to the soil, the antenna formed of a meta material, a measurement circuit disposed within the housing and operatively connected to the antenna, the circuit configured to measure impedance at a plurality of different frequencies using the antenna as a sensor electrode, a wireless interface disposed within the housing and operatively connected to the antenna and configured for wireless communications over the antenna at one or more communications frequencies, and a power source disposed within the housing and operatively connected to the measurement circuit and the wireless interface. The measurement circuit is configured for self-calibration using a known impedance. The plurality of different frequencies are within a range of about a few hundred KHz to about a few hundred MHz. The one or more communication frequencies may be higher than a sensing frequency and in a few hundred MHz range. The sensor may include a diplexer operatively connected to the antenna.

According to another aspect, a method for acquiring measurement data may include providing a sensor, the sensor comprising: a housing, (b) an antenna disposed on the outside of one of the faces of the housing exposed to the soil, the antenna formed of a meta material, (c) a measurement circuit disposed within the housing and operatively connected to the antenna, the circuit configured to measure impedance at a plurality of different frequencies using the antenna as a sensor electrode, (d) a wireless interface disposed within the housing and operatively connected to the antenna and configured for wireless communications over the antenna at one or more communications frequencies, (e) a power source disposed within the housing and operatively connected to the measurement circuit and the wireless interface, wherein the measurement circuit is configured for self-calibration using a known impedance. The method may further include measuring impedance at a plurality of different frequencies using the antenna as a sensor electrode to provide measurement data and wirelessly communicating the measurement data using the wireless interface. The method may further include determining soil moisture using the measurement data. The method may further include determining total ionic concentration using the measurement data. The method may further include performing a self calibration of the measurement circuit using the known impedance.

DETAILED DESCRIPTION OF THE PREFERRED EMBODIMENTS

The present invention is described with respect to various embodiments. It is to be understood that the present invention is not to be limited to or by the disclosed embodiments.

Figure 1A:
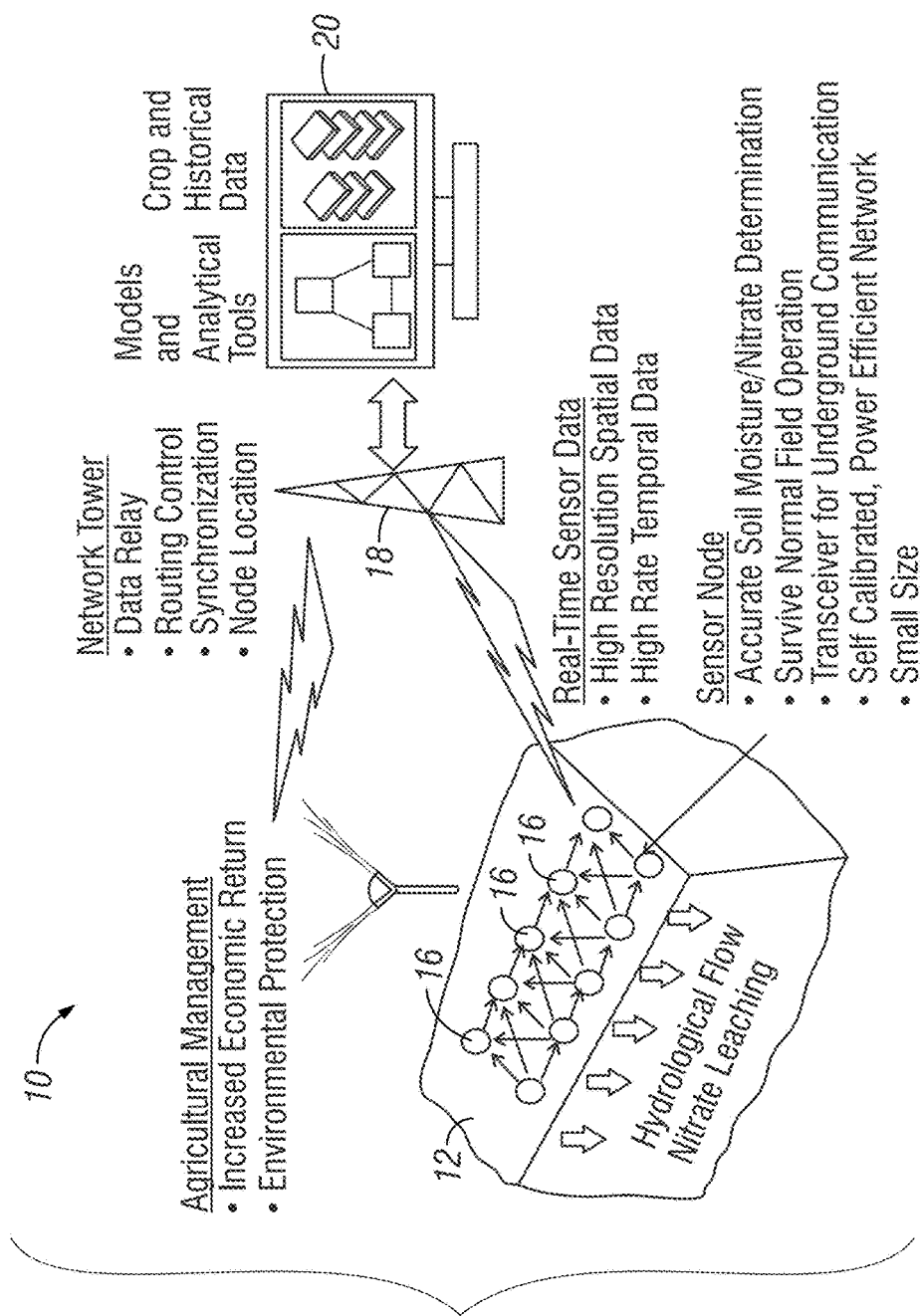
FIG. 1A is an illustration of a soil sensor network.

As shown in FIG. 1A, a system 10 is provided which includes a field 12 in which there is a sensor network 14 of multiple sensors 16. The sensor network 14 provides real-time sensor data including high resolution spatial data and high rate temporal data. Each sensor 16 preferably provides accurate soil moisture and nitrate determinations. Each sensor 16 preferably is robust enough to survive normal field operations. Each sensor 16 includes a transceiver for underground communication, is self-calibrating, has a small size and is power efficient. Data from the sensor network 14 may be communicated via a telecommunications network to a computer 20. The telecommunications network may include one or more network towers 18 and the telecommunications may provide for data relay, routing control, synchronization, node localization, and other functions. The computer 20 may be programmed to execute instructions stored on a non-transitory computer readable storage medium to provide functions such as models and analytical tools and to capture or use crop and historic data. Information such as the results from the application of analytical tools may be communicated over the telecommunications network to crop producers, land managers, or others to assist in agricultural management in order to support objectives such as increasing economic return, protecting the environment or other functions.

Figure 1B:
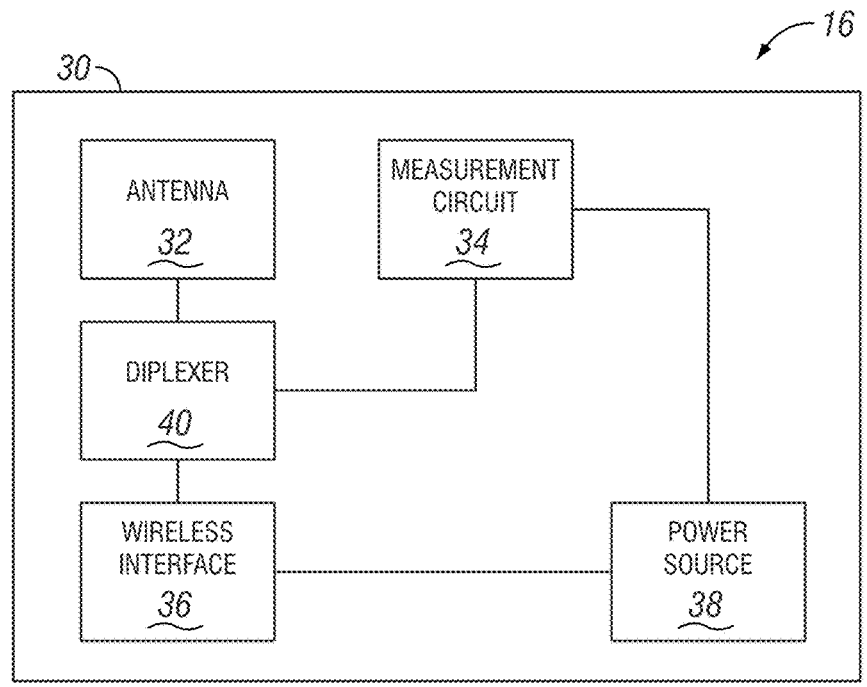
FIG. 1B is a block diagram of a soil sensor.

As shown in FIG. 1B, each sensor 16 has a housing 30. There is an antenna 32 disposed within the housing 30. The antenna 32 design is a meta-material design. A measurement circuit 34 is also disposed within the housing 30 and operatively connected to the antenna 32. The measurement circuit 34 is configured to measure impedance at a plurality of different frequencies using the antenna 32 as a sensor electrode as will be later explained herein. The measurement circuit 34 is preferably configured for self-calibration using a known impedance. A wireless interface 36 is disposed within the housing and operatively connected to the antenna 32 and is configured for wireless communications over the antenna 32 at one or more communication frequencies. A power source 38 is also disposed within the housing 30 and is operatively connected to the measurement circuit 34 and the wireless interface 36. A diplexer 40 may be used as will be later explained herein.

Impedance Measurement at Multiple Frequencies

The task of measuring soil content determination can be broken down broadly into three steps:
1. Measuring the unknown impedance of sensor which is embedded in the soil whose properties are to be determined;
2. Calculating the permittivity of soil using the measured impedance value;
3. Determining the soil moisture content from the permittivity values.

Reflection based impedance measurement is commonly used in TDR systems. [7], [27]. If reflection occurs at known frequencies, then accurate multi-frequency impedance measurement is possible. In our case we work with the frequency range of 1-50 MHz, generated by a microprocessor controlled phase lock loop (PLL). The reason for choosing this range of frequencies is that at lower frequencies the variations in capacitance and conductance of the sensor electrode are more pronounced, while at higher frequencies the variations in sensor electrode capacitance and conductance at different frequencies are lesser.

For transmission line with characteristic impedance $Z_0$ and load impedance $Z_L$, the coefficient of reflection, the ratio reflected and incident voltage signals, satisfies the formula [25]:

$$\Gamma_L = \frac{V_r}{V_i} = \frac{Z_L - Z_0}{Z_L + Z_0}. \quad (1)$$

Figure 2:
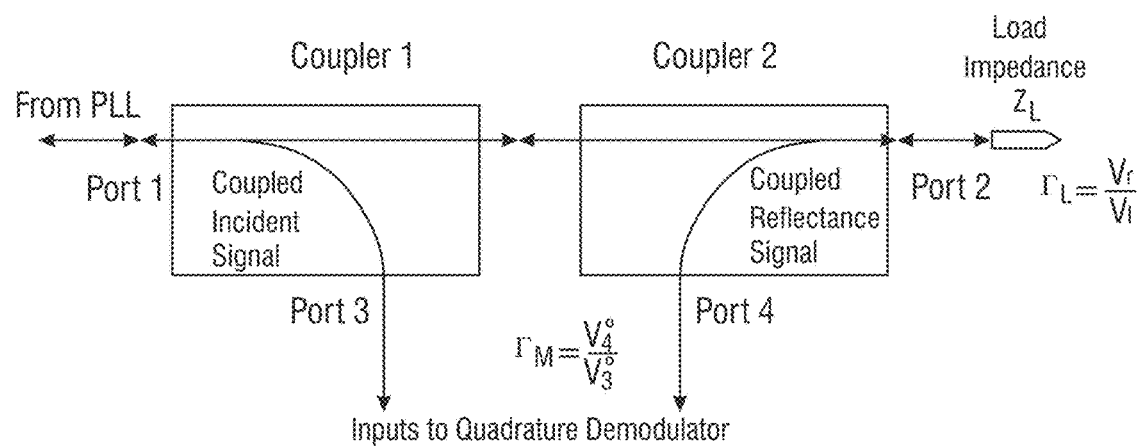
FIG. 2 is a directional coupling of incident and reflected signals.

$V_r$ and $V_i$ are sinusoidal signals reflected from an incident upon the load impedance respectively (see FIG. 2). For a micro-strip transmission line, $Z_0$ is substantially a constant and depends on the width of the transmission line and permittivity of the pcb substrate. We have designed $Z_0$ to be 50 ohms. Thus, if we make accurate measurements of $V_r$ and $V_i$, we can calculate the value of $Z_L$. To measure sinusoidal $V_r$ and $V_i$, we need to measure amplitudes and phases of $V_r$ and $V_i$. To make these measurements, incident and reflected signals, which are on the same transmission line, have to be separated. This can be done efficiently using a pair of directional couplers. A directional coupler is a device that can be used to couple a small fraction of the signal flowing in a particular direction on a transmission line to its output port. The signal flowing in other direction is not coupled. Two directional couplers are connected to the main line as shown in FIG. 2. One coupler couples the incident signal, while the other couples the reflected signal to its output port; coupling occurs through the process of induction, while the end, left versus right, chosen for terminations decides the nature of coupling, incident versus reflected.

Since the couplers are not point objects, there always is a finite distance between the point at which load is connected to the line and the point where signal coupling takes place. This means that the coupled signals at ports 3 and 4 are gain/phase shifted relative to the incident signal, $V_i$ and reflected signal, $V_r$ respectively. Since this shift depends on the frequency and the length of the transmission line between the coupler and the load impedance, this shift can be accounted for by proper calibration. In order to find a relationship between the ratio of reflected and incident signals at the load $$\left(\Gamma_L = \frac{V_r}{V_i}\right)$$

and the ratio of coupled reflected and incident signals at the ports 4 versus 3

$$\left(\Gamma_m = \frac{v_4^O}{V_3^O}\right),$$

we treat the combined system of two couplers and the transmission line as a four port network, with the ports numbered as shown in FIG. 2, where the source is port 1 and the load is port 2; port 3 couples with the incident signal and port 4 couples with the reflected signal. Owing to the fact that the outputs and inputs of such a 4-port network are bi-linearly related, it has been shown in [25] that the measured value of reflection coefficient, $\Gamma_m$ and the reflection coefficient at the load, $\Gamma_L$ are related by a bilinear transformation:

$$\Gamma_m = \frac{V_4^O}{V_2^O} = \frac{a\Gamma_L + b}{c\Gamma_L + 1} \quad (2)$$

where a, b and c are constants for this 4-port network while $V_4^O$ and $V_3^O$ are output voltage signals from port 4 and port 3 respectively. This implies that 3 measurements of $\Gamma_m$ at three different loads (or equivalently three different $\Gamma_L$'s) will give us 3 equations in 3 unknown calibration constants a, b and c. For ease of calculation we can chose these three known load impedances to be $\infty$ (open-circuit), 0 (short-circuit) and $Z_0$ (matched load), with the corresponding load reflection coefficients being $\Gamma_{L1}$=1; $\Gamma_{L2}$=−1; $\Gamma_{L3}$=0 respectively. The equations in 3 unknowns can be solved by solving the matrix:

$$\begin{bmatrix} \Gamma_{L1} & 1 & -\Gamma_{L1}\Gamma_{m1} \\ \Gamma_{L2} & 1 & -\Gamma_{L2}\Gamma_{m2} \\ \Gamma_{L3} & 1 & -\Gamma_{L3}\Gamma_{m3} \end{bmatrix} \begin{bmatrix} a \\ b \\ c \end{bmatrix} = \begin{bmatrix} \Gamma_{m1} \\ \Gamma_{m2} \\ \Gamma_{m3} \end{bmatrix}.$$

The constants a, b, c can then be calculated using:

$$\begin{bmatrix} a \\ b \\ c \end{bmatrix} = \begin{bmatrix} \Gamma_{L1} & 1 & -\Gamma_{L1}\Gamma_{m1} \\ \Gamma_{L2} & 1 & -\Gamma_{L2}\Gamma_{m2} \\ \Gamma_{L3} & 1 & -\Gamma_{L3}\Gamma_{m3} \end{bmatrix}^{-1} \begin{bmatrix} \Gamma_{m1} \\ \Gamma_{m2} \\ \Gamma_{m3} \end{bmatrix}.$$

Once we know the values a; b and c, we can use these values and the measurement of $\Gamma_m$ at an unknown load to infer $$\Gamma_L = \frac{b - \Gamma_m}{c\Gamma_m - a}, \quad (3)$$

when an unknown impedance with reflection coefficient $\Gamma_L$ is presented as the load. This value of $\Gamma_L$ can then be used to calculate the unknown load $Z_L$, by applying Equation 1.

Measurement of Signal Amplitude and Phase Method 1: Using Gain and Phase Detector IC For accurate measurement of $\Gamma_m$, it is important to make an accurate noise free measurement of $V_4^O$ and $V_3^O$. $V_4^O$ and $V_3^O$ are signals of a same applied frequency, $\omega$. These signals are sent as inputs to the Gain and Phase detector IC. The Gain and Phase detector generates 2 DC voltages in the range 0-1.8 V which correspond to the phase and gain ratios of the reflected and incident signals respectively.

The gain detector signal is described as follows:

The Gain and Phase detector IC has a series of logarithmic amplifiers which convert the input signals to a compact decibel scale output. Two such identical chains of logarithmic amplifiers are built in, each driven by signals of similar waveforms but at different levels (incident upon and reflected from soil). Since subtraction in logarithmic domain corresponds to a ratio in linear domain, the resulting output becomes $$V_{mag} = V_{slp} \log(V_{ref}/V_{inc}) = \text{magnitude}(V_1^O/V_2^O)$$

Where $V_{ref}$ and $V_{inc}$ are signals reflected from an incident upon soil, $V_{mag}$ is the output corresponding to the magnitude of signal level difference and Vslp is the slope which has the value of 30 mV/dB for this particular IC (AD8302 from Analog Devices).

The phase detector signal is described as follows:

The built-in phase detector is an exclusive-OR style phase detector which detects the zero-crossings of the incident and reflected signals. It has the form:

$$V_{phs} = V_{pslp}(\text{Phase}(V_{ref}) - \text{Phase}(V_{inc})) = \text{Phase}(V_4^O/V_3^O))$$

Where Vpslp is the phase slope in mV/degree and is equal to 10 mV/deg for the IC under consideration.

Method 2: Using Quadrature Demodulator

Figure 3:
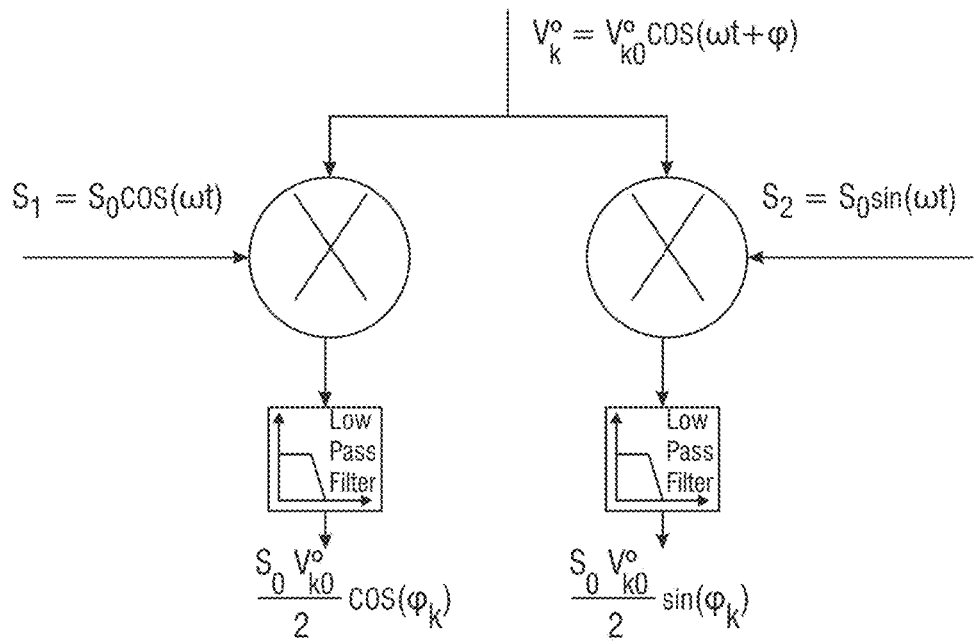
FIG. 3 is a quadrature demodulator which is used to calculate signal amplitude and phase.

Another method for accurate measurement of $\Gamma_m$, is to send the incident and reflected signals coupled to the outputs of coupler as input to a Quadrature Demodulator to extract their in-phase and quadrature phase components. A quadrature demodulator is essentially a pair of mixers which multiplies its input by a pair of sinusoids that are identical except their phases are 90 degrees apart, $S_1 = S_0 \cos(\omega t)$ and $S_2 = S_0 \sin(\omega t)$. Letting $V_k^O = V_{kO}^O \cos(\omega t + \phi_k)$ denote the port-k output (k=3; 4) that is fed as input to the quadrature demodulator (see FIG. 3), we have:

$$S_1 * V_k^o = \frac{S_0 V_{k0}^o}{2}(\cos(\phi_k) + \cos(2\omega t + \phi_k)), \text{ and}$$

$$S_2 * V_k^o = \frac{S_G V_{k0}^o}{2}(\sin(\phi_k) + \sin(2\omega t + \phi_k)).$$

On low pass filtering these two mixer outputs, their high frequency terms are rejected and the two outputs are the in phase component:

$$I_k = \frac{S_0 V_{k0}^o}{2}(\cos(\phi_k)), \quad (4)$$

and the quadrature-phase component, $$Q_k = \frac{S_0 V_{k0}^o}{2}(\sin(\phi_k)). \quad (5)$$

Then the ratio of amplitudes of $V_4^O$ and $V_3^O$ is calculated using:

$$\frac{V_{40}^o}{V_{30}^o} \sqrt{\frac{I_4^2 + Q_4^2}{I_3^2 + Q_3^2}}. \quad (6)$$

On the other hand, the phase difference $\phi_4 - \phi_3$ between $V_4^O$ and $V_3^O$ is given by:

$$\phi_4 - \phi_3 = \tan^{-1}\left(\frac{Q_4}{I_4}\right) - \tan^{-1}\left(\frac{Q_2}{I_3}\right). \quad (7)$$

The outputs of the quadrature demodulator/Gain and Phase detector are received by the microprocessor through an inbuilt Analog to Digital Converter (ADC). The microprocessor performs the calculations stated above to accurately determine $$\Gamma_m = \frac{V_4^O}{V_3^O}.$$

During the calibration phase, the microprocessor uses these values to calculate the coefficients a, b and c using the matrix-based computation discussed in previous section. During the measurement phase of an unknown load, it uses the a, b, c coefficients to find out the reflection coefficient $\Gamma_L$ for the unknown load using Equation 3. The $\Gamma_L$ value is then used to determine the unknown load impedance $Z_L$ using Equation 1. For quadrature demodulation, AD8333 from Analog Devices has been used.

Switching System for Self-Calibration

Figure 4:
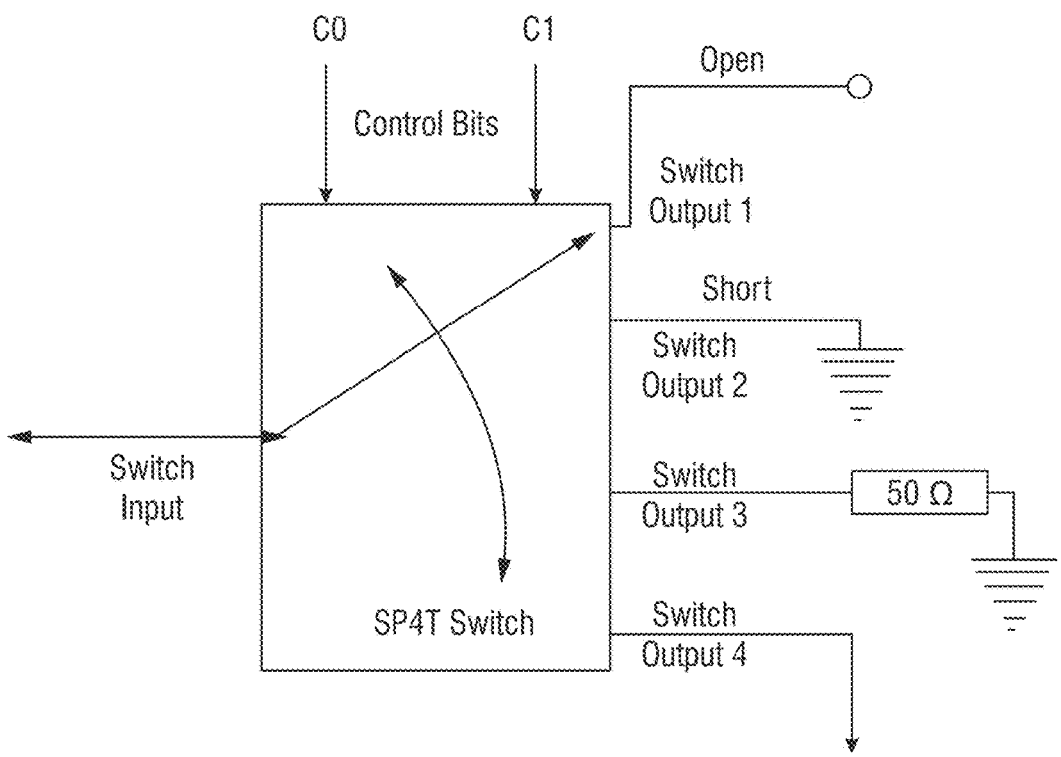
FIG. 4 is self-calibration using SP4T switch.

As seen in previous section, for sensor calibration we need the measurements on a set of three known impedances in order to account for the non-colocation of the load impedance and the coupler output ports. In order to make the sensor a self-calibrating system, we have designed a switching mechanism using a Single-Pole-4-Throw (SP4T) switch. An SP4T switch has a two bit control signal which controls the connection of input RF port to one of the four output ports (see FIG. 4). The control signal is programmed by the microprocessor, at the beginning of each sensing event, to cycle through all the four values. Once the control signal has swept through the values 00 (open-circuit), 01 (short-circuit) and 10 (matched load), we calculate the calibration constants a, b and c. For the measurement of unknown impedance, the control signal is changed to 11. Using the $\Gamma_m$ for this measurement and the calculated a, b, c values, we calculate $\Gamma_L$ which is then used to calculate $Z_L$.

Transceiver Multi-Power Modes

Figure 5:
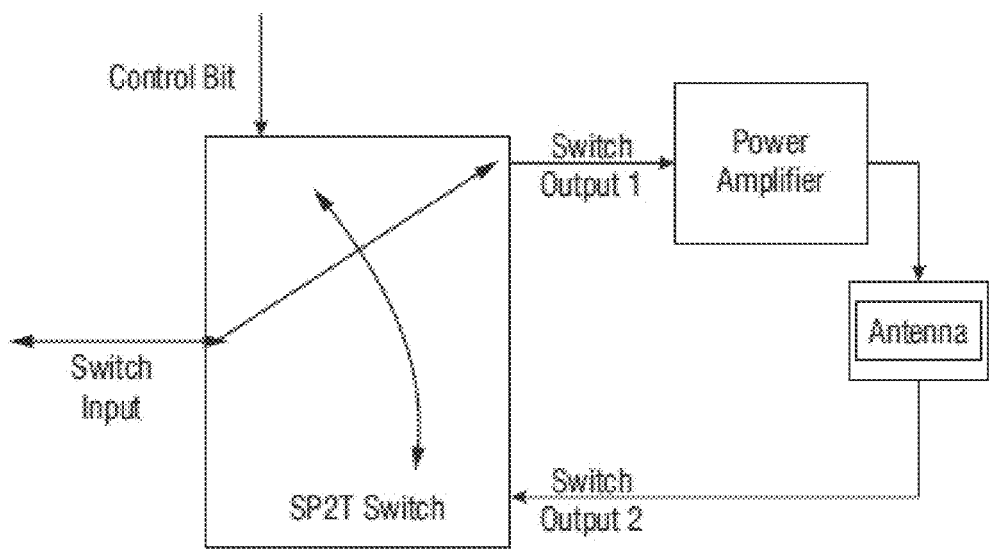
FIG. 5 is an implementation of different power modes in transmission and reception.

According to [13], an energy-efficient MAC can be implemented if an additional higher power transmission mode, called ping, and an additional lower power receiver sensitivity mode, called drowsy is included (besides the usual normal and sleep modes). [11] showed that using these extra power modes, a more energy-efficient MAC and networking can be executed resulting in over 65% of energy savings. We implement these multiple power modes by using a system shown in FIG. 5, where a Single-Pole-2-Throw (SP2T) switch is placed in between the transceiver and the antenna. During a transmission in the ping mode, the SP2T connects the transmitter to a power amplifier which amplifies the signal by 15 dB before feeding it to the antenna. During reception, the SP2T feeds the signal directly to the receiver, bypassing the power amplifier. Besides, the off-the-shelf transceiver CC1110 from Texas Instruments that we use already has an in-built receiver with the additional drowsy mode for a "low-powered listening" during wake-up synchronization which is initiated at the same time as the generation of a "high-powered ping" by a neighboring node (see [13] for details of the MAC).

Electrodes Diplexed to Act as Antenna

Figure 6A:
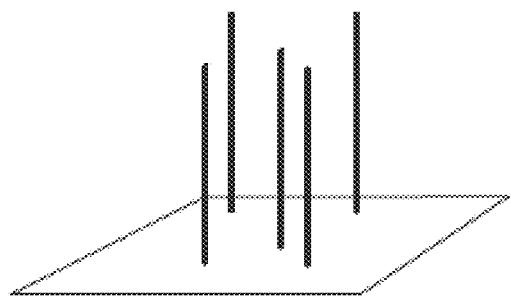
FIG. 6A is a five prong monopole antenna that doubles up as a sensor electrode.
Figure 6B:
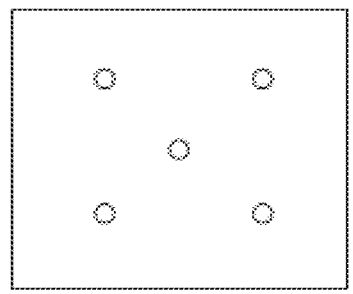
FIG. 6B is a top view of FIG. 6A.
Figure 7:
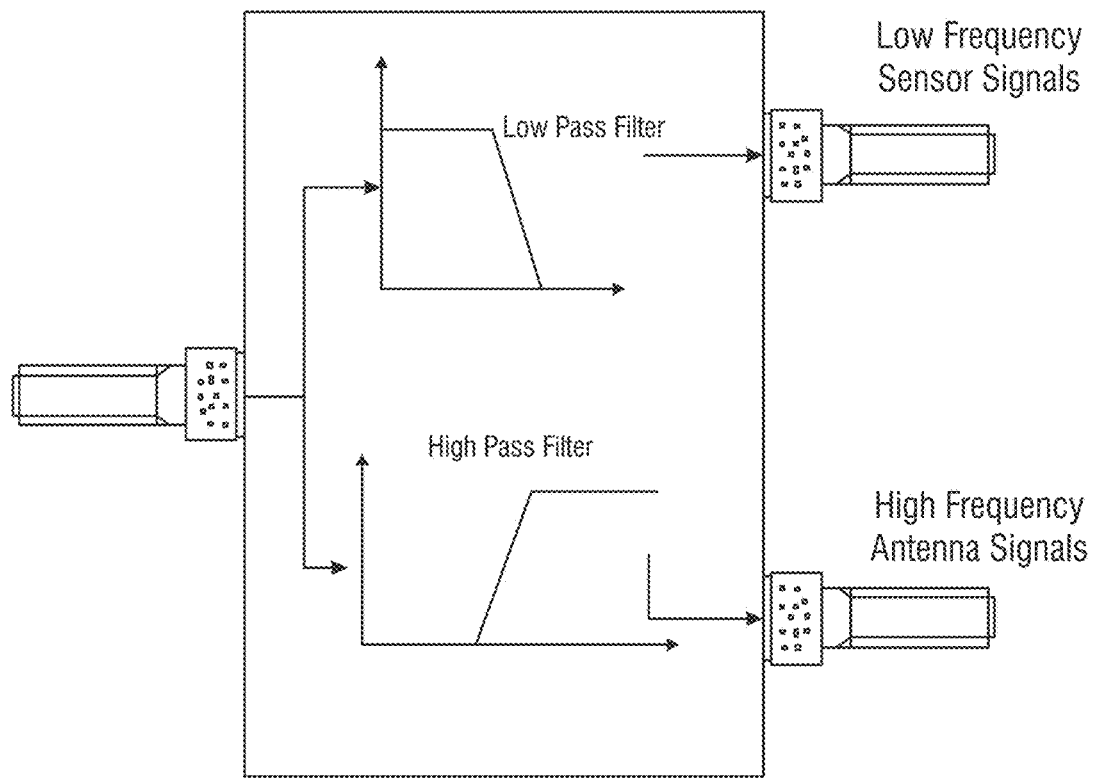
FIG. 7 is a diplexer configuration.

Once the microprocessor has the soil impedance measurement, it needs to transmit it to the receiver. For this purpose, and to reduce the size of the sensor node, we have designed the sensor electrodes to double up and act as an antenna with the help of a diplexer. Initial measurements were done with a quarter wavelength monopole antenna which, at 433 MHz frequency, is approximately 17 cm in length and has been mounted as a center prong on a copper ground plane. Apart from this center prong that acts as a monopole antenna mounted on a copper ground plane, there are 4 more prongs surrounding the central prong (see FIG. 6) which act as the ground pins for the antenna as well as the sensor electrode. In this 5 prong sensor, the center prong acts as the antenna at the transmission frequency of 433 MHz and as the positive electrode at the sensing frequencies of 1 MHz to 50 MHz. The remaining 4 prongs act as the ground in the antenna and as the negative electrode in the sensor measurements. Since the transmission and the sensing occur at two different frequencies, 433 MHz versus 1-50 MHz respectively, it is possible to separate the two frequency paths using a diplexer (see FIG. 7). A diplexer has a high pass path with the transmission frequency in its pass-band and the minimum sensing frequency in its stop-band. It also has a low pass path with the transmission frequency in its stop band and the minimum sensing frequency in its pass band. The 5-prong antenna is not the final choice for the sensing electrode and an improved CRLH antenna described further is used due to its reduced size.

Overall Sensor Architecture

Figure 11:
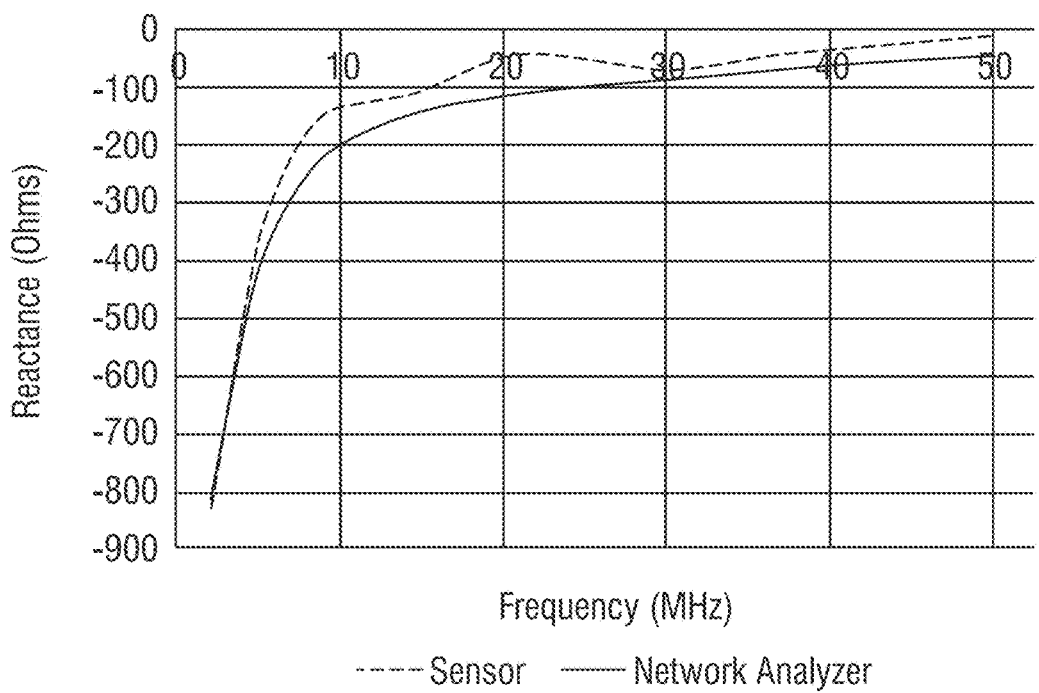
FIG. 11 is an imaginary part of soil impedance as measured by on-board sensor (solid) and network analyzer (dashed).

The complete sensor architecture consisting of microprocessor, transceiver, phase-lock-loop (PLL) for sinusoid generation, directional coupler, gain and phase detector quadrature demodulator, SP4T and SP2T switches, power amplifier, low-pass-filter and diplexer is as shown in FIG. 11. When the system starts, the first step by the microprocessor is to program the PLL to the desired frequency of operation. The microprocessor, that also has an inbuilt transceiver, is CC1110 from Texas Instruments. In the first step, the I2C interface of the programmable PLL (CDC903 from Texas Instruments) is programmed to generate 2 frequencies $\omega_1$ and $\omega_2$, where $\omega_1$ is the measurement frequency, in the range of 1-50 MHz, with $\omega_2=4\ \omega_1$. The $\omega_1$ signal is sent through the transmission line towards the SP4T switch. The $\omega_2$ (=4 $\omega_1$) signal is sent to the quadrature demodulator which internally converts these signals to 2 signals $S_1$ and $S_2$ that are at 90 phase difference from each other. These signals are used by the quadrature demodulator to convert the outputs of the couplers into in-phase and quadrature-phase components.

Although the frequency range for measurement is chosen as 1-50 MHz, the architecture itself is extendible to higher frequencies as well. The signal generator CDC913 from Texas Instruments has the capability to generate signals up to 200 MHz. Hence the same architecture can be used for impedance measurements till 200 MHz and more if a different phase-locked loop that can generate higher frequencies is used. For this application though, 50 MHz is a good range as beyond that noticeable change in impedance with our sensing electrodes was not observed.

The SP4T switch which is used for calibration gets its control bits from the microprocessor. In the calibration mode, a sequence of 00, 01 and 10 is sent to the SP4T switch. Thus, the transmission line is connected to open, short and matched load in the consecutive cycles of SP4T switching control signal. Once calibration is completed the control signal is set to 11 which sets the connection to the unknown load which for our application is a soil sample.

The incident and reflected waves are coupled to the output ports of the directional couplers located along the transmission line. The output signals are passed on to the inputs of a gain and phase detector (AD8302 from Analog Devices). The outputs of gain and phase detector are received by the microprocessor through an in-built 12-bit ADC (Effective number of bits is 10.8). The microprocessor calculates Amplitude and Phase of the incident and reflected waves. In the calibration mode, these values are used to calculate the coefficients a, b and c using the matrix method discussed in a previous section. In the measurement mode, it uses these coefficient values to find out the reflection coefficient $\Gamma_L$ for an unknown load. The $\Gamma_L$ value is then used to determine the unknown impedance $Z_L$ using Equation 1.

Experimental Validation

Figure 9:
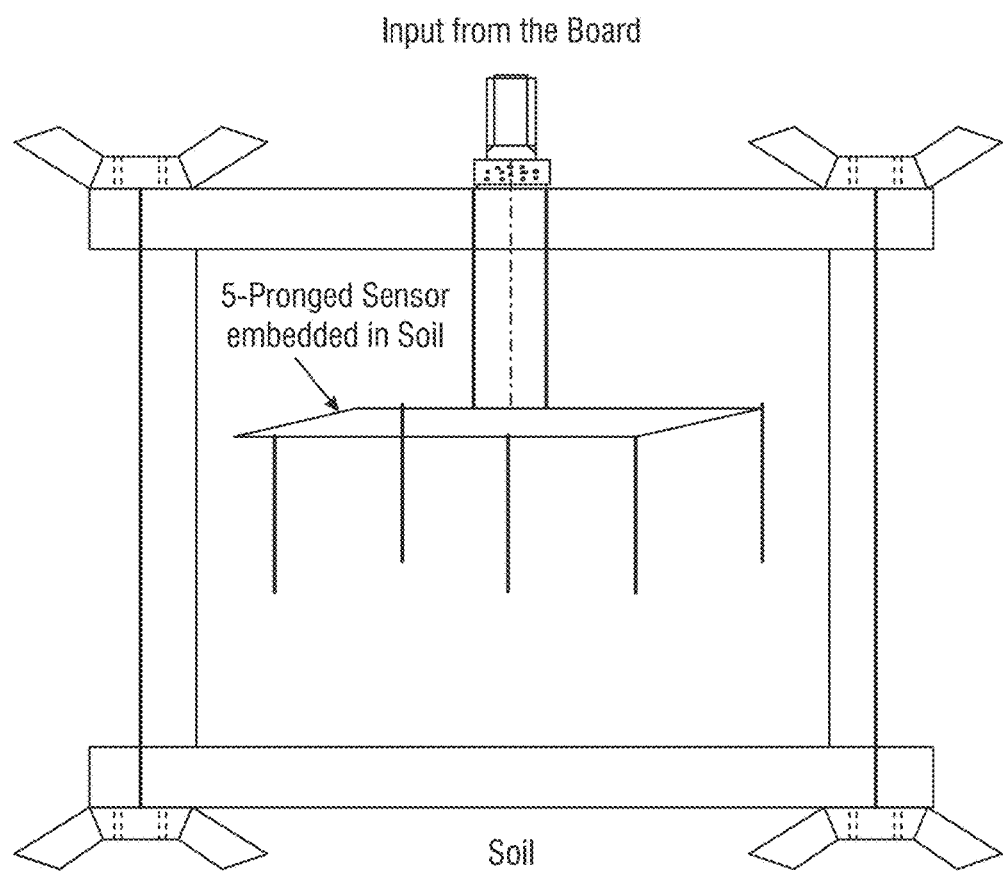
FIG. 9 is an experimental setup.
Figure 10:
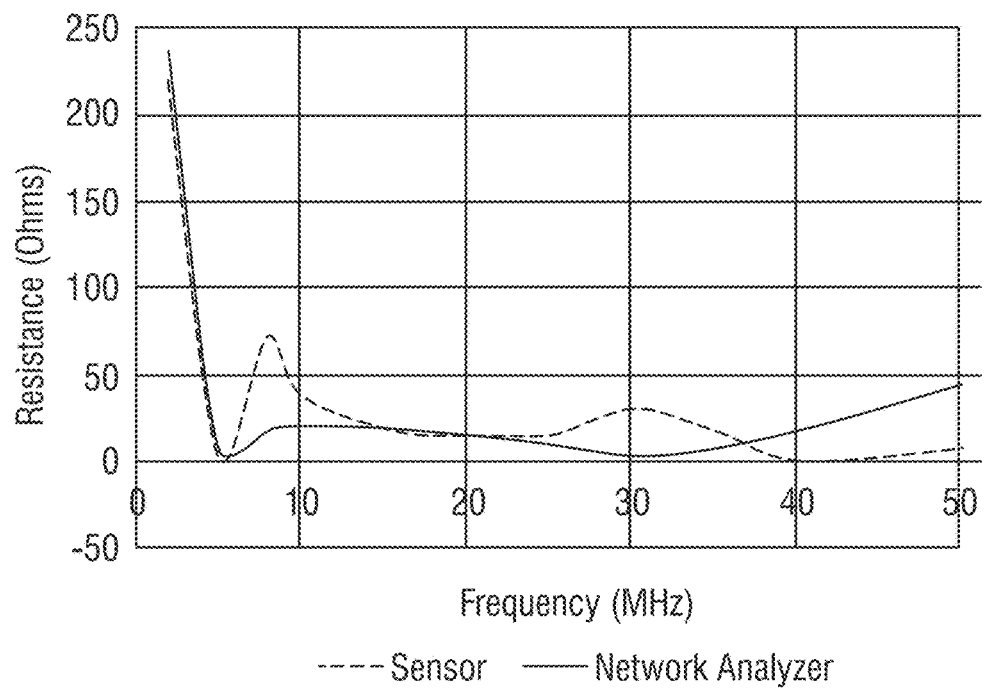
FIG. 10 is a real part of soil impedance as measured by on-board sensor (solid) and network analyzer (dashed).

A cylindrical fixture was constructed using acrylic material to hold the soil with the 5-prong sensor embedded into the soil (see FIG. 9). To connect the sensor to the on-board circuit, the fixture was fitted with an SMA (Sub-Miniature version A) port at the top whose one end was connected to the SP4T switch mounted on the pc board and the other end, which is interior to the cylindrical fixture, was connected to the 5-prong sensor/antenna. The cylindrical fixture with 5-prong sensor inside was filled with the clarion loam soil that was collected from the top 0.50 m layer at the Iowa State University Agronomy Research Farm situated in Boone County, Iowa. For validation purposes, the soil impedance was measured by the on-board sensor that we designed and also by a Network Analyzer (HP8714ES). This 5-prong sensor with soil contained between the prongs, acts as the unknown load. The data recorded by the on-board circuit is transmitted to a receiver which first calculates the a, b and c calibration constants and then calculates the soil impedance using Equations 3 and 1. The real and imaginary parts of impedance measured using the on-board sensor showed a good match with those measured using the network analyzer in the range 1-50 MHz (see FIGS. 10 and 11), with a maximum error of less than 10%. No such in-situ sensors, capable of scanning real as well as imaginary parts of impedance over a frequency range, and with accuracy, have been reported in literature.

Using Dielectric Mixing Model to Find the Volume Fractions of the Constituents

One way to use impedance measurements to obtain ionic concentrations is by treating the soil as a homogeneous medium and with various ionic concentrations as inclusions embedded into this medium. Such homogenizing methods have been used in the past to obtain dielectric mixture models [20]. A generalized model proposed in [20] considers a mixture of n different types of ellipsoidal particles with different concentration, orientation and distribution that are embedded in a host with permittivity $\epsilon_{host}$. The proposed equation for effective mixture permittivity, $\epsilon_{eff}$, in this model is:

$$\epsilon_{eff} = \epsilon_{host} + \frac{\frac{1}{3}\sum_{j=1}^{n} f_j(\epsilon_j - \epsilon_{host})\sum_{i=1}^{3}\frac{\epsilon_{host}}{\epsilon_{host} + N_{ji}(\epsilon_j - \epsilon_{host})}}{1 - \frac{1}{3}\sum_{j=1}^{n} f_j(\epsilon_j - \epsilon_{host})\sum_{i=1}^{3}\frac{N_{ji}}{\epsilon_{host} + N_{ji}(\epsilon_j - \epsilon_{host})}},$$

where $f_j$ is the volume fraction of $j^{th}$ inclusion, $N_{ji}$'s are the depolarization factors of $j^{th}$ component along $i^{th}$ coordinate (they depend on the shape of the inclusion) and $\epsilon_j$ is the permittivity of $j^{th}$ component. For different frequencies, permittivities of individual ions also vary due to dielectric relaxation. Many such relaxation models like Debye relaxation, Havriliak-Negami relaxation etc. are present in literature [11]. Debye relaxation model is given by the equation:

$$\epsilon = \epsilon' + j\epsilon'' = \epsilon_\infty + \frac{\epsilon_S - \epsilon_\infty}{1 + j\omega\tau},$$

where $\epsilon_s$ the permittivity of the molecule at very low frequencies, $\epsilon_\infty$ is the permittivity at very high frequencies and $\tau$ is the relaxation time which is defined as the time required by the molecular dipole to reach new equilibrium when a time varying external Electric field is applied.

Noting that all $\epsilon$'s in the mixing-model are functions of frequency as captured by their relaxation models, it follows from the above model that if the $\epsilon$ values of individual constituents are known at different frequencies, and an accurate measurement of permittivity of the mixture is made at multiple-frequencies, it is possible to calculate individual constituent concentrations by solving the mixing model. For a host mixed with n additional components, we need at least n equations in n unknown constituent concentrations. These n equations can be obtained by making n number of measurements of $\epsilon_{eff}$ at multiple frequencies. (At different frequencies, $\epsilon$'s of constituents are different, and so the same mixing model yields different equations at different frequencies.)

The in-situ soil impedance sensor described above has the ability to make measurements of soil permittivity from 1 MHz to 50 MHz. Dependence of nitrate and chlorides on soil permittivity has previously been demonstrated through laboratory work in [4] using multi-frequency dielectric spectra from 1-14 MHz. Thus, using our sensors, it is possible to determine constituent concentration by applying the classic dielectric mixing and relaxation models combined with permittivity measurements at different frequencies.

Experimental Results on Determination of Nitrate Concentration

Figure 12:
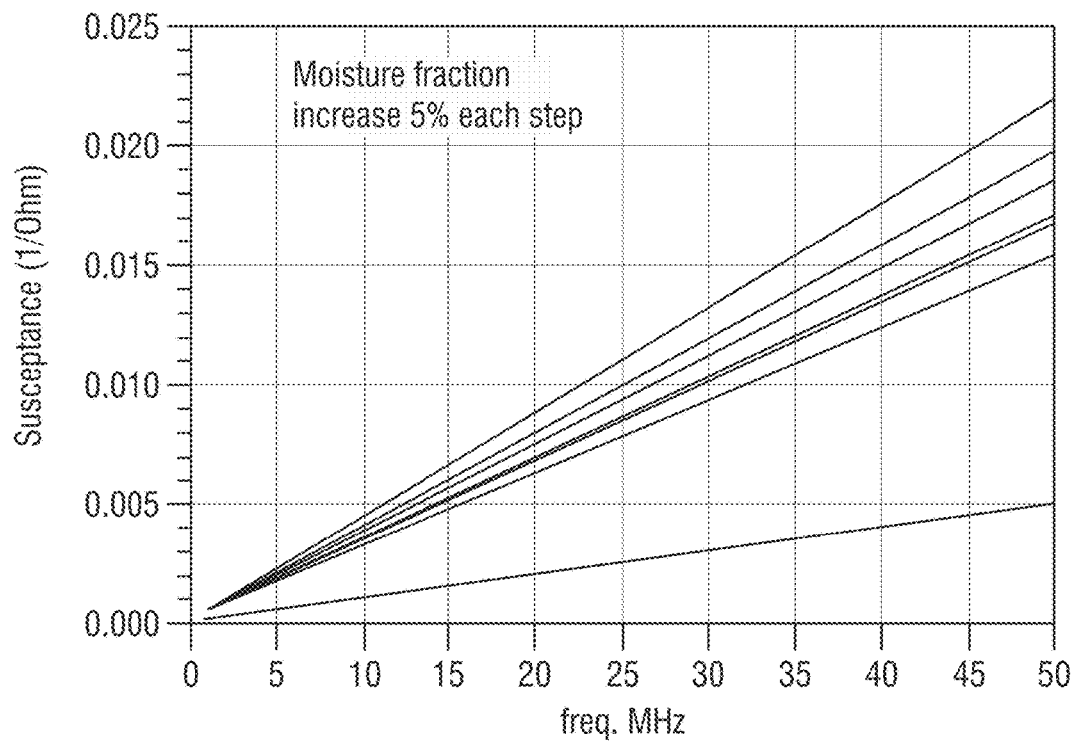
FIG. 12 is susceptance variations with frequency at different concentrations of sodium nitrate.
Figure 13:
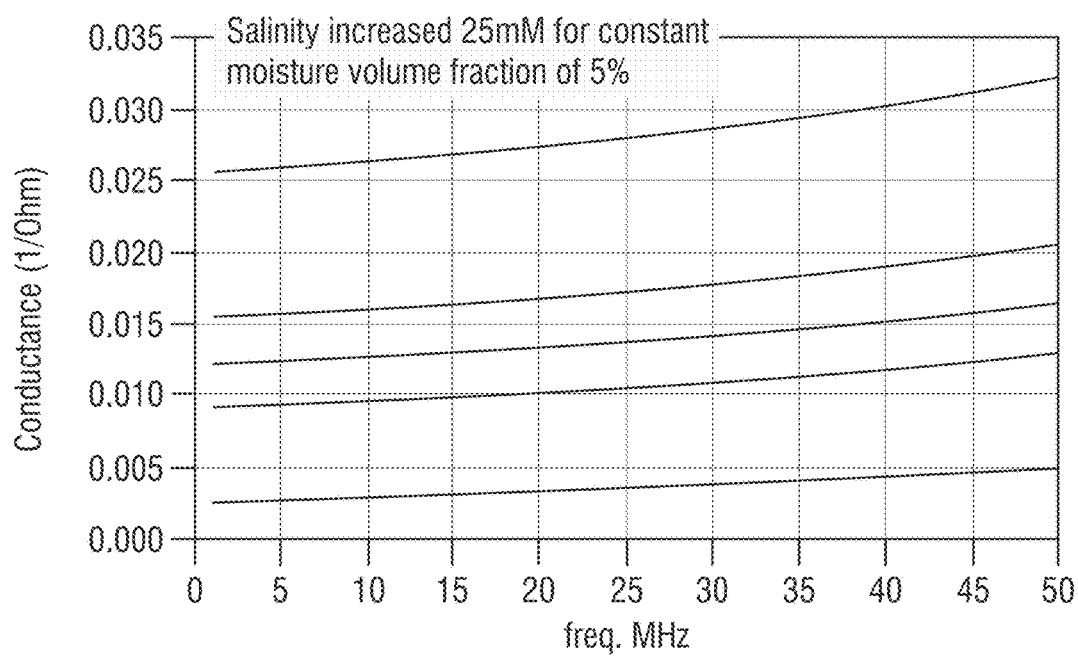
FIG. 13 is conductance variations with frequency at different concentrations of sodium nitrate.

To experimentally verify our approach, sodium nitrate solution was incrementally added to a soil sample which was collected from the top 0.50 m layer at the Iowa State University Agronomy Research Farm situated in Boone County, Iowa. As the sodium nitrate solution is incrementally added to the soil, the permittivity of the soil starts to increase (FIGS. 12 and 13). This results in increasing capacitance (hence susceptance) and conductance of the soil dielectric mixture. Here we assume that the fraction of soil bulk does not change during the course of the experiment.

Figure 14:
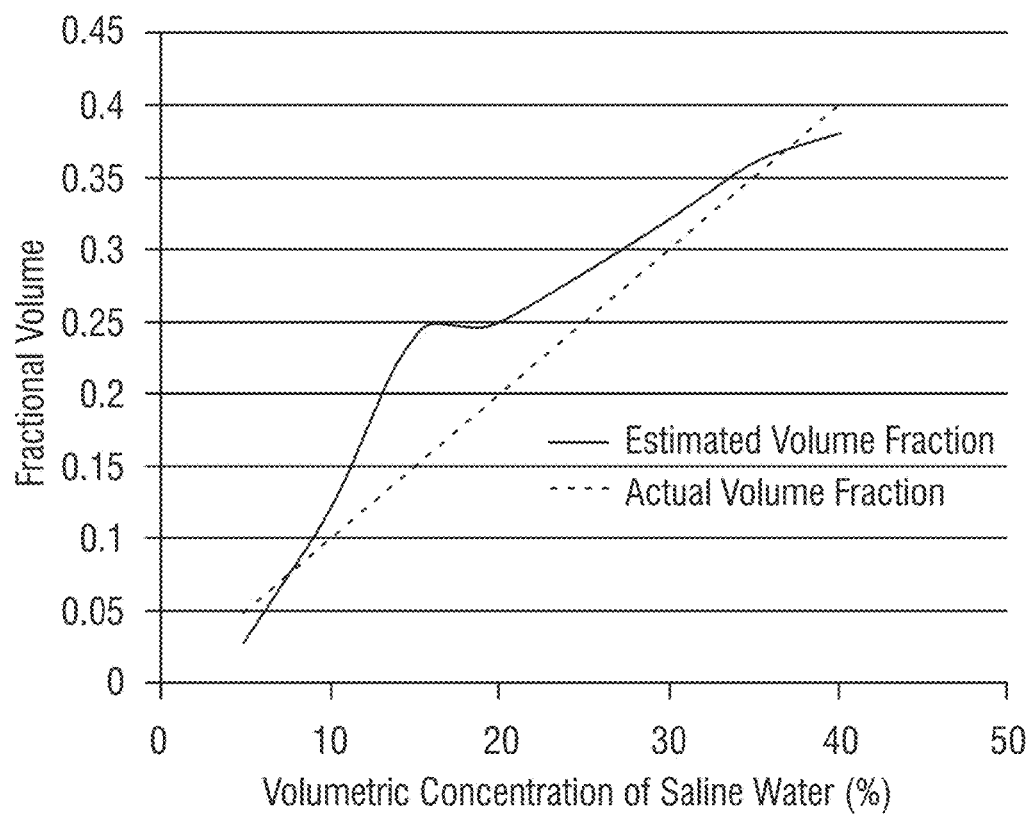
FIG. 14 is estimation of saline water fractional volume.

On applying the mixing models to the above values of capacitance (that is proportional to real part of permittivity [18]) and conductance (that is proportional to imaginary part of permittivity), close estimates to actual values of the saline water (error within 12% for whole range) concentration were obtained (See FIG. 14).

The above results demonstrate a proof-of-concept of employing mixing models to separate out fractions of the constituents. Further work is needed to build on this proof-of concept in order to accurately determine the concentrations of individual ions such as nitrates, phosphates and sulphates. This may include additional refinement of the sensor such as inclusion of electrophoresis to physically separate out the ions before taking the dielectric measurements.

Thus, an on-board architecture for an in-situ, wireless, energy efficient, robust, accurate and self-calibrating soil moisture and nutrient sensor with inbuilt wireless transmission and reception capability has been presented, designed, fabricated and validated. The on-board sensor was shown to have good accuracy (within 10% for both real and imaginary part of impedance for 1-50 MHz frequency range) which was comparable to a Network Analyzer. The accurate multi-frequency measurements on soil impedance can provide information not only about soil moisture content but also about overall ionic concentrations. The soil saline water content was measured within 12% error range. This shows that there is enough window of improvement in application of model as well as improving the accuracy of sensing system itself through further refinement of the circuit so as to reduce the effect of parasitics.

Antenna Considerations

In a generic precision agriculture approach (see FIG. 1), intra- and inter-field variabilities are characterized using a network of sensor nodes spread over a large area. Each sensor node sends local information about the properties of the soil surrounding it. All the information collected is sent to a central node which processes the information and takes necessary control measures towards irrigation and fertilization. The in-situ, buried sensors require an efficient transceiver system that can provide enough power to overcome the losses incurred during signal transmission in soil and also have an antenna that is small enough to maintain a compact size of the sensor.

Our previous work on soil-sensing, that uses modified quarter wavelength monopole type electrodes as probes [19], [32], has proven that multi-frequency impedance measurements of a soil mixture have the capability to provide information about the soil moisture together with the concentration of different ions like nitrates in soil. In [19] we presented a self-calibrating, multi-frequency dielectric sensor for combined moisture and soil ion concentration sensing, while in [32] we showed how dielectric-mixing models can be reasoned to analyze the multifrequency dielectric measurements to estimate the soil moisture and overall ion concentrations. We have also shown that the quarter wavelength monopole antenna can be used dually as a sensor probe as well as a transmitting/receiving antenna. This was achieved by separating the low-frequency sensing path from high frequency transmission path using a diplexer.

A limitation of the 5-prong monopole electrodes discussed earlier is their size, which at carrier frequency of 433 MHz must be 17 cm standing vertically on a horizontal ground plane (Note we chose a carrier frequency of 433 MHz, as although a lower frequency will offer a superior range, the size of the antenna would become even larger). An antenna height of 17 cm is clearly not very convenient for underground applications as the in-situ nature of agricultural application calls for a small embedded antenna. Integration of our soil sensors with a microstrip antenna, a flat structure, can make the sensors more compact and more usable for in-situ operation. For wireless interfacing, planar microstrip antennas exist and are widely used owing to their small size, low cost and ease of integration. Such antennas have also been used to dual as sensing probes [29] in soil-moisture sensing applications.

A microstrip patch antenna/probe combination has also been investigated as part of our own earlier research [18]. The input impedance of the microstrip patch was shown to vary with surrounding nitrate and moisture concentrations and was used to detect the changes in moisture and nitrate concentrations in soil. While flattened in vertical dimension, regular microstrip patch antennas still suffer the size issue since they are not small enough in size in the other two dimensions (e.g. 11.5 cm×9.3 cm at 433 MHz carrier frequency). The 24 cm×20 cm size of a flattened regular patch antenna size is an improvement over a monopole, but the size is still much larger compared to the rest of the circuit.

This work presents a metamaterial inspired small flat antenna that provides a practical solution for an underground application. The main contributions of this work are:
1) A new metamaterial inspired CRLH antenna that reduces the antenna size by about 93% of the original patch antenna.
2) Application of the CRLH antenna as the sensing element by using a diplexer that allows the use of the CRLH patch as a probe at low frequencies and as transmitting/receiving antenna at higher frequencies.
3) Mapping the measured input impedance of the CRLH patch embedded in its surroundings to its complex permittivity.
4) Improvement in the accuracy of the sensor by accounting for the influence of the parasitic capacitances in our measurements.

The new antenna design along with an inbuilt self-calibrating mechanism makes our sensor suitable for underground application such as soil nitrate management or for a hand held device such as in food safety or microbial detection applications. A multi-power mode transceiver system has been designed to support the implementation of an energy efficient medium-access-control (MAC) protocol. An overview of our multi-frequency impedance measurement system is provided as well as a discussion on design and fabrication of CRLH patch. Experimental validation of real and imaginary parts of impedance measurements over the frequencies of 1-50 MHz is also provided.

Overview: Multi-Frequency Impedance Measurement

Figure 15:
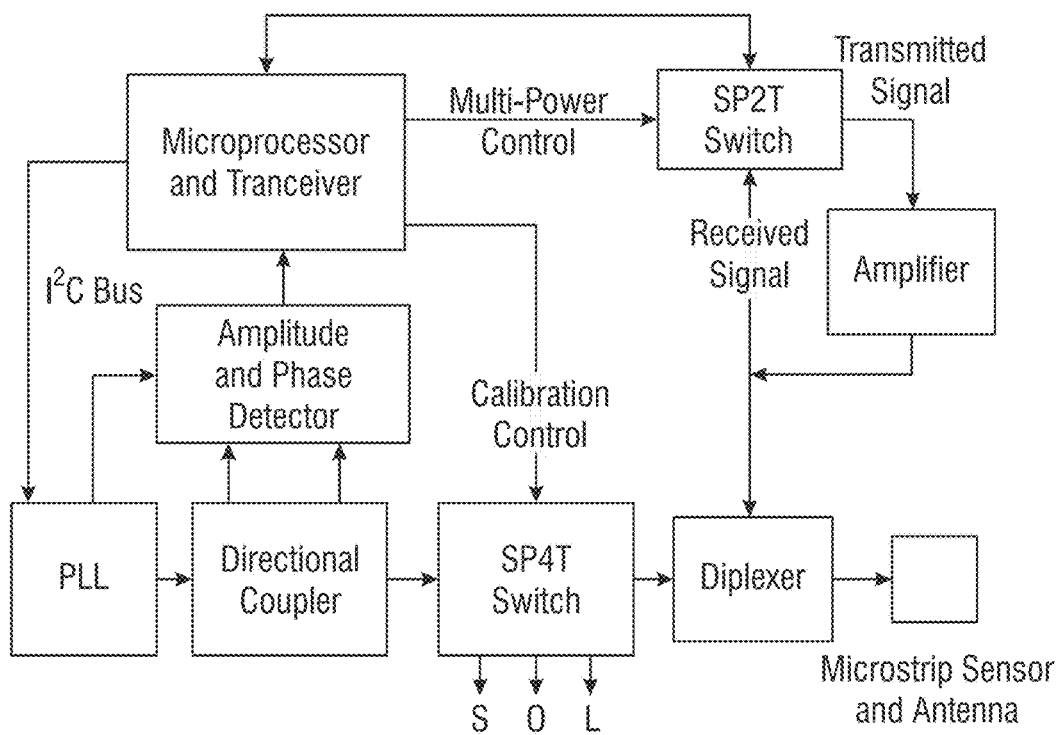
FIG. 15 is a dielectric sensor architecture.

We have recently designed and tested a dielectric measurement based soil impedance sensor that can sense at multifrequencies (hence accurate & reliable), is self-calibrating (hence robust), possesses wireless interface (hence can be located in-situ), and is also energy-efficient [19]. The sensor architecture, consisting of probe and antenna, directional couplers, phase locked loop (PLL), amplitude and phase detector, switches/diplexer, microprocessor & transceiver, is shown in FIG. 15.

Upon startup, the microprocessor programs the I2C interface of the programmable PLL to generate a signal of known frequency. The frequency of the probing signal is chosen in the range of 1-50 MHz, and is chosen so that a significant variation in real and imaginary part of the soil impedance can be observed. While the lower limit of 1 MHz on frequency is put by the architecture of the sensor, the upper limit of 50 MHz was obtained experimentally as above this value the soil reactance becomes close to zero, An slight increase in this value can provide more data points to analyze but beyond that no useful information on soil ionic concentration can be extracted from it although it may be helpful for other application where spectroscopy can detect constituents. The probing signal is sent through the transmission line to the SP4T switch, which is programmed by the microprocessor to select among a set of known loads plus the unknown soil-sample load. The incident and reflected signals to and from the load are captured using the directional couplers and are passed on to a detector which calculates the amplitude and phase of each signal and passes this information to the microprocessor for further processing and transmission via antenna. These values are received by the microprocessor through an in-built 12-bit ADC. In the calibration mode, when the loads are of known values, these values are used to calculate the calibration parameters that correlate the reflection coefficients (ratio of reflected to incident) measured at the couplers to those at the load through a 3-parameter bilinear transform, In the measurement mode, when the load is the soil-sample, these calibration parameters are used to find out the reflection coefficient for an unknown load from its value measured at the directional coupler, through the same bilinear transform whose parameters were determined in the calibration mode. The reflection coefficient value is then used to determine the unknown load impedance that contains the information about the soil contents (moisture and nutrients).

Figure 16:
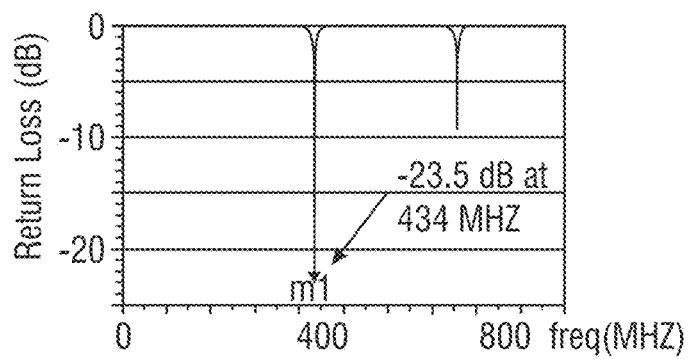
FIG. 16 illustrates dimensions of the CRLH patch.
Figure 17:
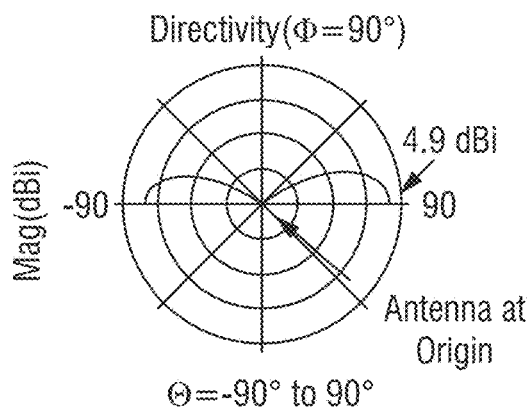
FIG. 17 is the electric field lobes for the CRLH antenna.

The resistive versus reactive soil impedance measurements over 1-50 MHz by our sensor are shown in FIGS. 16 and 17. The accuracy of our in-situ sensor is confirmed against the measurements from a lab equipment, a network analyzer, HP8714ES (plots also shown in the same figures). A more than 90% accuracy over the range of 1-40 MHz in soil reactance was observed.

CRLH Patch Antenna/Sensor-Probe

The propagation constant for a signal traveling in soil is given in [2] by:

$$\gamma = \sqrt{j2\pi f \mu (2\pi f (\epsilon'' + j\epsilon))} = \alpha + j\beta \quad (8)$$

where f is the transmission frequency, $\alpha$ is the attenuation factor while $\beta$ is the phase constant. On solving this equation for $\alpha$ we get:

$$\alpha = 2\pi f \sqrt{\frac{\mu\epsilon}{2}\left(\sqrt{1 + \left(\frac{\epsilon''}{\epsilon'}\right)^2} - 1\right)}, \quad (9)$$

where $\epsilon'$ and $\epsilon''$ are the real and imaginary parts of soil permittivity. It can be observed that the attenuation factor $\alpha$ increases linearly with frequency (and so loss exponentially with frequency). Thus, increasing the frequency, f, increases the losses in the transmission signal and decreases the antenna range. On the other hand, lowering the frequency (to counter path losses) increases the width, W as well as the length, L of a patch antenna as can be seen from the equations (10) and (11) in which f appears in the denominator [2].

$$W = \frac{c}{2f\sqrt{\frac{\epsilon_r+1}{2}}}, \quad (10)$$

$$L = \frac{c}{2f} + 2\Delta L. \quad (11)$$

Here, $\epsilon_r$ is the relative permittivity of the substrate and $\Delta L$ is the length correction factor given in [2] by:

$$\Delta L = 0.412h \frac{\epsilon_{\mathit{eff}} + 0.3\frac{W}{h} + 0.264}{\epsilon_{\mathit{eff}} - 0.258\frac{W}{h} + 0.8}. \quad (12)$$

In (12), h is the height of the dielectric substrate and $\epsilon_{\mathit{eff}}$ is the effective permittivity due to multiple media (substrate dielectric and air) involved, and is given in [2] by:

$$\epsilon_{\mathit{eff}} = \frac{\epsilon_r+1}{2} + \frac{\epsilon_r-1}{2}\left[1+12\frac{h}{W}\right]^{-\frac{1}{2}}. \quad (13)$$

Since $\sqrt{\epsilon_r+1}$ appears in denominator of (10), it seems that the size of the antenna can be reduced, by using a very high permittivity substrate. But a problem is that the antenna efficiency also goes down with increasing substrate permittivity.

For the transmission frequency of 433 MHz, the length and width were calculated to be 24 cm and 20 cm respectively for a relative substrate permittivity) of 3.55 and substrate height of 0.813 mm. The ground plane size was decided based on the analysis presented in [5] as: (L+6h)×(W+6h)=24.5 cm×20.3 cm. Since the sensor circuitry can be designed to fit into a relatively smaller size (7 cm×5 cm for our on-board design), the antenna size is the limiting factor in overall sensor size. To address this technological challenge, we look beyond the standard materials, towards the so called metamaterials.

Metamaterials are specially constructed designs which offer electric and magnetic properties opposite of materials found in nature such as negative permittivity and permeability. This creates a possibility of engineering a small-sized metamaterials matching network between the antenna and the surrounding medium so that the energy stored in the near field is radiated away. Size improvements of factor greater than 10 compared to standard antennas have been observed in [6], [36], [35]. Authors in [6] discuss a composite right-left handed (CRLH) transmission line based antenna, with potentially improved efficiency for small patch antennas. Another such implementation has been reported in [29]. Here, we present another design based on a standard CRLH structure [6] that can also be dueled as an underground sensing element (see FIG. 18 and its fabrication in FIG. 21).

Figure 18:
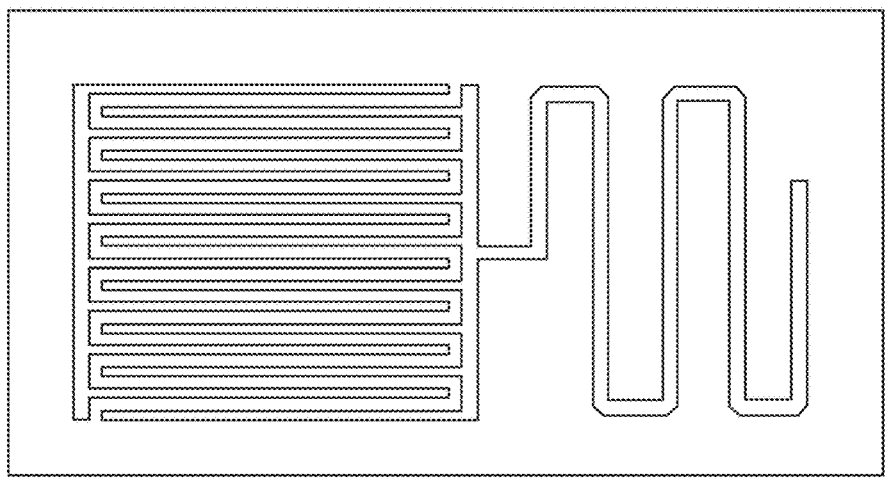
FIG. 18 is the figurative representation of CRLH antenna
Figure 19:
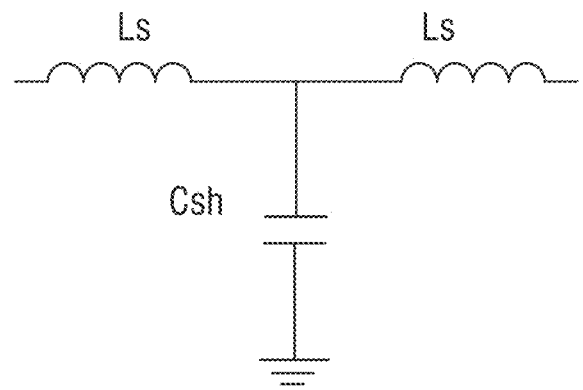
FIG. 19 is a unit cell structure for a common right handed transmission line.
Figure 20:
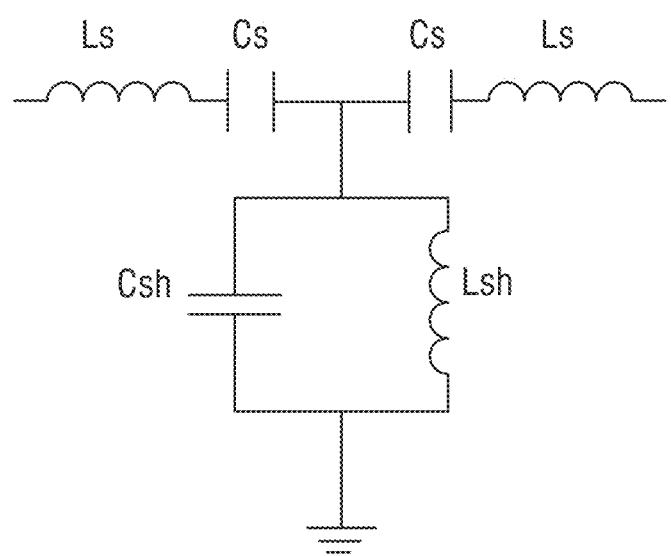
FIG. 20 is a unit cell structure for a CRLH transmission line.

Resonance in CRLH type antenna can be understood by considering the unit-cell structure in a small patch resonating structure. For a regular transmission line, the well-known distributed parameters structure is depicted by a series inductance followed by a shunt capacitance as shown in FIG. 19, Such a structure supports only the right-handed wave propagation which means that the phase shift observed in an incident signal along the length of structure is positive [31]. In a CRLH structure, this phase shift can be either positive or negative due to the effect of apparent negative permittivity and permeability in the structure. One type of structure that can achieve this apparent negative permittivity/permeability is shown in FIG. 18, with its distributed parameter model depicted in FIG. 20, which contains additional series capacitances and shunt inductances. For such a structure, the series impedance is given by:

$$Z_{series} = j\left(2\pi f L_s - \frac{1}{2\pi f C_s}\right). \quad (14)$$

Similarly, shunt reactance is given by:

$$Y_{shunt} = j\left(2\pi f C_{sh} - \frac{1}{2\pi f L_{sh}}\right). \quad (15)$$

It has been shown in [6] that better efficiency for a CRLH antenna is achieved when series and shunt parts of the structure resonant at same frequency which is given by:

$$\omega_{resonant} = 2\pi f_{resonant} = \frac{1}{\sqrt{L_s C_s}} = \frac{1}{\sqrt{L_{sh} C_{sh}}} \quad (16)$$

Figure 8:
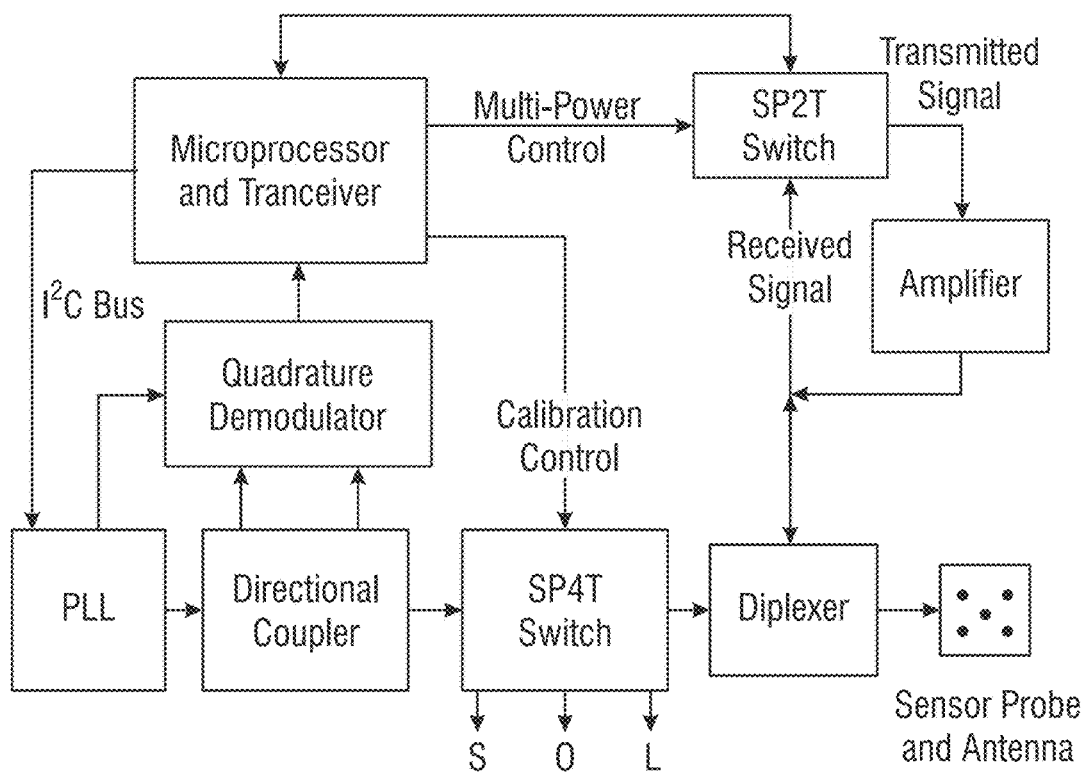
FIG. 8 is a proposed sensor architecture.

In our antenna, series capacitance is introduced by the inter-digitized finger capacitor while shunt inductance was realized using a meander shaped microstrip stub (see FIG. 18 and its fabrication in FIG. 8). The CRLH antenna structure was simulated using ADS (Advanced Design System, Agilent Technologies) software and resonance was observed for both series and shunt structures at the desired frequency of interest (433 MHz).

Figure 21:
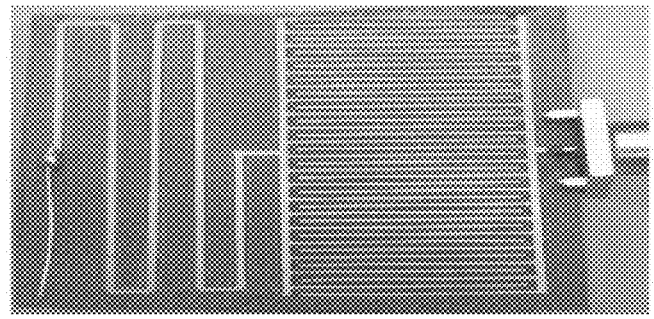
FIG. 21 is fabricated CRLH patch antenna.
Figure 22:
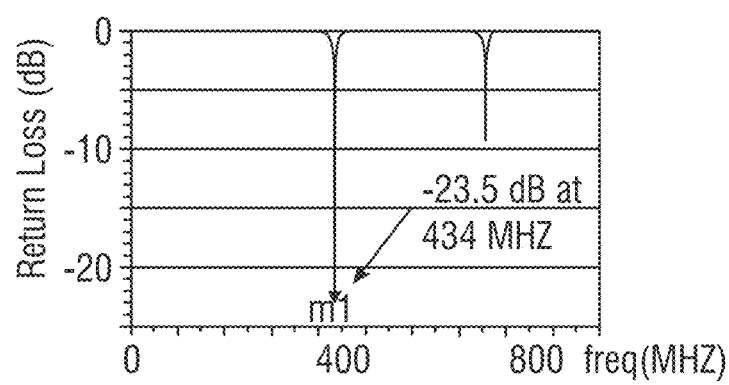
FIG. 22 is a return loss for the fabricated antenna.

The antenna is fabricated on a pc board (see FIG. 21) with relative substrate permittivity 3.55, thickness 0.813 mm and dielectric loss tangent of 0.002 (Rogers R4003C laminate). From simulations it was observed that although 5% improvement in efficiency can be achieved by reducing dielectric constant to 2, the size requirement goes up by 60%. The thickness was chosen to fit the antenna structure in a compact volume in order to keep a small size for the overall sensor, Hence, the chosen values give a good balance between efficiency, availability and size for a patch structure. The metal on the top has a thickness of 0.0355 mm and a conductivity of 5.8e7 S/m (copper). The dimensions of the antenna are shown in FIG. 18 while FIG. 21 shows the actual fabrication. Resonant frequency of 433 MHz is demonstrated in the reflectivity plot of FIG. 22. The antenna dimensions are 3 cm×2 cm which is 93.3% smaller in area than the standard patch antenna of size 11.5 cm×9.3 cm).

| Real Permittivity | Imaginary Permittivity | Total Soil Loss (dB) | Air Range (m) |
|---|---|---|---|
| 5 | 0 | −20.11977416 | 2429.112311 |
| 5 | 1 | −24.75190827 | 1425.085396 |
| 5 | 2 | −29.25552044 | 848.5164789 |
| 5 | 3 | −33.53841942 | 518.2213868 |

-continued

| Real Permittivity | Imaginary Permittivity | Total Soil Loss (dB) | Air Range (m) |
|---|---|---|---|
| 5 | 4 | −37.55665477 | 326.2898503 |
| 5 | 5 | −41.30425815 | 211.9451072 |

Range of the Metamaterial Inspired Antenna Buried 0.25 m Under Ground

The built in transceiver system in our sensor can transmit at a maximum power of 18 dBm while the receiver has a sensitivity of −110 dBm, meaning a 128 dB path-loss can be tolerated. The range of our antenna can be calculated using Frii's equation for path loss:

$$P_r(dB) = P_t(dB) + G_t(dB) + G_r(dB) + 20\log_{10}\left(\frac{c}{4\pi fr}\right) + 20\log_{10}(e^{-\alpha r})$$

where $P_r$ and $P_t$ are received and transmitted powers, $G_t$ and $G_r$ are transmitting antenna gain and receiving antenna gain, and r is the distance between transmitting and receiving antenna. In our setting, $P_r$=−110 dBm, $P_t$=18 dBm, $G_r$=$G_t$=0 dBm, f=433 MHz, and $\alpha$ is determined using Equation 9 by substituting $\epsilon'$ and $\epsilon''$ values from Table I, which also lists the calculated ranges r, assuming that antenna is buried 0.25 m below the soil surface. If needed, we can raise the transmission power from 18 dBm to 25 dBm, thereby increasing the range by roughly a factor of 1.7 (e.g., from 211 to 345).

The real part of soil permittivity is dominated by saline water concentration, whereas the imaginary part of the soil permittivity is governed by the concentration of free ions. According to [4], maximum value of nitrate concentration in a typical clay-loam field is 200 $mg^{-1}L^{-1}$ which results in a soil permittivity of approximately 5+j5 at 20% by volume moisture content for frequencies above 14 MHz. Hence, we have used this value as the worst case scenario for making range calculations; the other range values are calculated at the same moisture level but lower nitrate concentrations so the soil permittivity ranges from 5+j to 5+5j, yielding range values between 2429 m and 211 m. It can be seen that even for large values of nitrate concentration in soil (which cause the imaginary part of relative permittivity to rise) while keeping the same moisture level, the antenna range remains 211 m. Thus, the proposed antenna can be effectively used to communicate with above the air satellite/base station located in the field while the sensors are buried 0.25 m below the ground.

Test Results

Comparison with Network Analyzer

The soil impedance was measured by our on-board sensor [19] and for comparison of its accuracy also by a Network Analyzer (HP8714ES). The CRLH patch sensing element, along with its surrounding medium, namely soil, presents itself as a load impedance to the sensor. The measurement data recorded by the on-board sensor is transmitted to a receiver which first calculates the calibration parameters and using those, calculates the unknown load of the surrounding soil. The imaginary part of impedance measured using the on-board sensor showed a better than 85% match with those measured using the network analyzer in the range 1-50 MHz while real part showed accuracy better than 70% for frequencies above 1 MHz. (see FIGS. 10 and 11).

Admittance Variation with Varying Moisture and Nitrate Conditions

FIGS. 25 and 26 show the variation in patch admittance with changing values of sodium nitrate solution. A 100 milli molar sodium nitrate solution was added in steps of 4% by volume increments to the soil that had sensor with the patch, acting as a probe (as well as antenna, at another frequency), buried into it. It was observed that the measured conductance (reciprocal of the real-part of impedance) of the patch increased as the concentration of sodium nitrate was increased in soil, whereas there was a much smaller variation in the susceptance (imaginary part of admittance, admittance is the reciprocal of impedance) value. This demonstrates that the accurate measurement of soil impedance (equivalently, admittance) using a microstrip patch sensing probe at multiple frequencies has the potential to successfully detect changes in ionic concentration in soil. The dielectric mixing models [20] that determine the permittivity of a mixture as a function of the composition and content of the mixture, together with the dielectric relaxation models [11] that determine the permittivity as a function of the frequency can be employed to estimate the concentrations of moisture versus nitrates versus air in the soil from the measurements, as is the case in [33].

CONCLUSION

An on-board self-calibrating multi-frequency dielectric sensor with small sized planar patch for sensing as well as wireless interfacing was designed, fabricated and validated against a network analyzer The sensor was shown to accurately measure the soil impedance at multiple frequencies over 1-50 MHz, with less than 15% error in reactance when compared to a bench top network analyzer (HP87I4ES). The impedances measured by the sensor is useful in estimating the contents of ionic concentration and moisture in soil. This work improves upon our previous work on underground soil moisture and nitrate sensing [32], [33] by reducing by almost 93% antenna dimensions thus allowing the design of a compact overall sensor size, making it suitable for field-deployment and handheld applications.

Transmission in lossy medium like soil requires a low frequency to be used for transmission. The low transmission frequency causes the antenna size to be significantly large [2]. Since flat antenna structures are most suitable for our application, we are developed a small microstrip patch antenna using composite right-left-handed metamaterials [6], [29]. The whole package with small antenna, impedance measurement system discussed herein and electrophoresis system to detect multiple ions can provide valuable information about soil properties in real time and is very beneficial for the environment.

The above dielectric spectroscopy and mixing-model based approach when combined with the in-situ sensors earlier provides a solution for accurate, real-time soil nitrate sensing which can prove hugely beneficial for agricultural production as well environment protection. Estimation of saline water concentration can be used to determine concentration of individual ions in the soil. Such work has previously been done for fluids using electrophoresis of ions dispersed in fluidic media [14], [26]. Similar efforts to detect various ions in soil is currently underway in our lab. Detection of various ions combined with overall conductivity of soil mixture has the potential to provide estimates about concentrations of different ions present. It is further contemplated that various different models may be used such as to relate the impedance of the sensor to the surrounding permittivity values. Such models can be applied to data obtained in this work to determine the permittivity of the surrounding soil, and the permittivity values at multiple frequencies can then be used to estimate ionic concentrations [32], [33].

Therefore a sensor has been disclosed along with related systems and methods. Although various specific embodiments have been disclosed the present invention contemplates numerous variations, options, and alternatives. Although various embodiments of a sensor have been described herein, the present invention contemplates numerous additional options, variations, alternatives, and improvements. This includes variations in the housing, the antenna, the structure and function of the measurement circuit, the wireless interface, the communication frequencies used, the measurement frequencies used, the antenna pattern(s) used, and other variations. Although the sensor may at times be described as a soil sensor it is to be understood that the sensor may be used in other types of medium in addition to soil.

Therefore the present invention is not to be limited to the specific embodiments described herein.

REFERENCES

[1] Abdul Mounem Mouazena; Josse De Baerdemaeker and Herman Ramonb. Towards development of on-line soil moisture content sensor using a fibre-type nir spectrophotometer. Soil and Tillage Research, 80(1-2):171-183, January 2005.

[2] Constantine A. Balanis. Antenna Theory Analysis and Design, Third Edition. Wiley Publications, Arizona State University, Arizona, 2005.

[3] Andrea Benedetto and Francesco Benedetto. Remote sensing of soil moisture content by gpr signal processing in the frequency domain. IEEE SENSORS JOURNAL, 11(10):2432-2441, October 2011.

[4] Giorgi Chighladze; Amy Kaleita; Stuart Birrell and Sally Logsdon. Estimating soil solution nitrate concentration from dielectric spectra using partial least squares analysis. Soil Science Society of America Journal, 76(5):1536-1547, November 2011.

[5] Christine Berggren; Bjarni Bjarnason and Gillis Johansson*. Capacitive biosensors. Electroanalysis, 13(3):173-180, March 2001.

[6] Tatsuo Itoh Christophe Caloz and Andre Rennings. Crlh metamaterial leaky-wave and resonant antennas. Antennas and Propagation magazine, IEEE, 50(5):25-39, October 2008.

[7] G. J. Gaskin and J. D. Miller. Measurement of soil water content using a simplified impedance measuring technique. Journal of Agricultural Engineering Research, 63(2):153-159, February 1996.

[8] Oshinski E. Huichun Xing; Jing Li, Liu; R. and R Rogers. 2.4 ghz onboard parallel plate soil moisture sensor system. In Sensors for Industry Conference, pages 35-38, 2005.

[9] Suat Irmak. Watermark granular matrix sensor to measure soil matric potential for irrigation management, 2006.

[10] Balendonck J. and M. A. Hilhorst. Application of an intelligent dielectric sensor for soil water content, electrical conductivity and temperature. In Instrumentation and Measurement Technology Conference, 2001. IMTC 2001. Proceedings of the 18th IEEE, pages 1817-1822, 2001.

[11] K. A. Klein J. Carlos Santamarina and Moheb A. Fam. Soils and Waves: Particulate Materials Behavior, Characterization and Process Monitoring. J. Wiley and Sons, J. Carlos Santamarina, Georgia Institute of Technology, 2001.

[12] Yan Songhua; Gong Jianya and Li Hanwu. Research on soil moisture sensor nodes and their placement in distributed sensor networks. In Distributed Computing and Applications to Business Engineering and Science (DCABES), 2010 Ninth International Symposium on, pages 165-168, 2010.

[13] Herman Sahota; Ratnesh Kumar and Ahmed Kamal. Performance modeling and simulation studies of mac protocols in sensor network performance. In Wireless Communications and Mobile Computing Conference (IWCMC), 2011 7th International, pages 1871-1876, 2011.

[14] F. Laugere, J. Bastemeijer, G. van der Steen, M. J. Vellekoop, P. M. Sarro, and A. Bossche. Electronic baseline-suppression for liquid conductivity detection in a capillary electrophoresis microchip. In Sensors, 2002. Proceedings of IEEE, pages 450-453, 2002.

[15] Manu S. Mannoor; Siyan Zhangb; A. James Linkb and Michael C. McAlpinea. Electrical detection of pathogenic bacteria via immobilized antimicrobial peptides. In Proceedings of the National Academy of Sciences of the United States of America, 2010.

[16] A. Manut and A. R. Nur Firdaus. Design, fabrication and testing of fringing electric field soil moisture sensor for wireless precision agriculture applications. In Information and Multimedia Technology, 2009. ICIMT '09. International Conference on, pages 513-516, 2009.

[17] Robinson D. A.; S. B. Jones; J. M. Wraith; D. Or and S. P. Friedman. A review of advances in dielectric and electrical conductivity measurement in soils using time domain reflectometry. Vadose Zone Journal, 2(4):444-475, November 2003.

[18] Gunjan Pandey, Ratnesh Kumar, and Robert J. Weber. Determination of soil ionic concentration using impedance spectroscopy. In Defense, Sensing and Security Conference, SPIE, Baltimore, Md., 2013.

[19] Gunjan Pandey, Ratnesh Kumar, and Robert J. Weber. A multifrequency, self-calibrating, in-situ soil sensor with energy-efficient wireless interface. In Defense, Sensing and Security Conference, SPIE, Baltimore, Md., 2013.

[20] A H Sihvola and J A Kong. Effective permittivity of dielectric mixtures. IEEE Transactions on Geoscience and Remote Sensing, 26(4):420-429, July 1988.

[21] H. A. Majid; N. Razali; M. S. Sulaiman and A. K. Aain. A capacitive sensor interface circuit based on phase differential method, 2009.

[22] G. J. Kluitenberg; T. Kamai and J. W. Hopmans. Design and numerical analysis of a button heat pulse probe for oil water content measurement. Vadose Zone Journal, 8(1): 167-173, February 2009.

[23] A. Valente, S. Soares, R. Morais, J. M. Baptista, and M. Cabral. Button heat-pulse sensor for soil water content measurements. In Sensor Device Technologies and Applications (SENSORDEVICES), 2010 First International Conference on, pages 180-182, 2010.

[24] G. Watson W. T.; Fluor Daniels; Richland W A; Holslin D.; Johansen F.; Stokes T.; Vargo and V. Verbinski. Results of modeling and experimental measurements for the design of a neutron surface moisture measurement sensor. In Nuclear Science Symposium, 1996. Conference Record., 1996 IEEE, pages 139-143, 1996.

[25] Robert J. Weber. Introduction to Microwave Circuits, Radio Frequency and Design Applications. IEEE Press Series on RF and Microwave technology, IEEE Press, ISBN 0-7803-4704-8, 2001.

[26] Yi-Chi Wei, Shin-Yu Su, Lung-Min Fu, and Che-Hsin Lin. Electrophoresis separation and electrochemical detection on a novel line-based microfluidic device. In Micro Electro Mechanical Systems (MEMS), 2012 IEEE 25th International Conference on, pages 104-107, 2012.

[27] B. Will and M. Gerding. A novel sensor design for the determination of dielectric profiles using time domain reflectometry. In Inst. of High Freq. Eng., Ruhr-Univ. Bochum, Bochum, Germany Gerding, M., pages 791-794, 2009.

[28] Yamamoto; Y. and A Ogawa. Novel soil-moisture-sensors applying thermal characteristics of soil and water. In Sensors, 2002. Proceedings of IEEE, pages 484-489, 2002.

[29] Wang Guang-ming Zhou Cheng and Liang lian gang. Novel zerothorder resonator antenna based on composite right/left handed (crlh) transmission line. In Cross Strait Quad-Regional Radio Science and Wireless Technology Conference (CSQRWC), 2011, pages 379-381, 2011.

[30] G. Kumar and K. P. Ray, Broadband Microstrip Antennas, Artech House Inc., 2003.

[31] Shaowei Liao, Jianhua Xu, Feng Wan, Wenxiang Wang, and Yubing Gong. Left-banded/right-handed transmission line subwavelength cavity resonators, IEEE ANTENNAS AND WIRELESS PROPAGATION LETTERS, VOL. 8, 2009,8(s):80-83, April 2009.

[32] Gunjan Pandey, Ratnesh Kumar, and Robert J. Weber. Real time detection of soil moisture and nitrates using on-board in-situ impedance spectroscopy. In IEEE System, Man and Cybernetics Society 2013, Manchester, UK, 2013.

[33] Gunjan Pandey, Ratnesh Kumar, and Robert J, Weber. Real time detection of soil moisture and nitrates using on-board in-situ impedance spectroscopy. In Defense, Sensing and Security Conference, SPIE, Baltimore, Md., 2013.

[34] Pichitpong Soontornpipit, Cynthia M. Furse, You Chung Chung, and Bryan M. Lin. Optimization of a buried microstrip antenna for simultaneous communication and sensing of soil moisture. IEEE TRANSACTIONS ON ANTENNAS AND PROPAGATION, 54(3): 197-800, March 2006.

[35] Richard W. Ziolkowski and Aycan Erentok. Metamaterial-based efficient electrically small antennas, IEEE Transactions on Antennas and Propagation, 54(7):21.13-2130, July 2006.

[36] Richard W Ziolkowski, Peng Jin, and Chia-Ching Lin. Metamaterial-inspired engineering of antennas. Proceedings of the IEEE, 99(I 0): 1720-1731, October 201 I.

[37] G. Pandey, R. Kumar and R J Weber. "A low RF-band impedance spectroscopy based sensor for in-situ, wireless soil sensing", IEEE Sensors Journal, 2014.

[38] G. Pandey, R. Kumar and R J Weber. "A low profile, low-RF band, small antenna for underground, in-situ sensing and wireless energy-efficient transmission" 11th IEEE International Conference on Networking, Sensing and Control, Miami, Fla., 2014.

[39] G. Pandey, R. Kumar, and R. Weber. Real time detection of soil moisture and nitrates using on-board in-situ impedance spectroscopy. 2013 IEEE International Conference on Systems, Man, and Cybernetics, Manchester, UK.

[40] G. Pandey, R. Kumar, and R. Weber. Detection and Estimation of Soil Nitrates and Chlorides Using Impedance Spectroscopy. ASA-CSSA-SSSA Annual meeting 2013, Tampa, Fla.

[41] G. Pandey, R Kumar, R. Weber. Design and Implementation of a self-calibrating, compact micro strip sensor for in-situ dielectric spectroscopy and data transmission, IEEE Sensors conference 2013, Baltimore, Md.

What is claimed is:

1. A soil sensor for emplacement and operation in situ in soil comprising:
    a housing having a surface to be exposed to soil;
    an antenna disposed on the surface of the housing, the antenna comprising
        a flat microstrip patch antenna;
    a measurement circuit disposed within the housing and operatively connected to the antenna, the circuit to measure impedance of soil at a plurality of different frequencies using the antenna as a sensor electrode using reflection—based spectral impedance/dielectric sensing at low RF band sensing frequencies;
    a wireless interface disposed within the housing and operatively connected to the antenna and configured for wireless communications over the antenna at one or more communications frequencies differentiated from the sensing transmissions from the antenna,
    so that a parameter related to impedance of soil can be derived using a plurality of impedance measurements at the plurality of different frequencies from the antenna in a sensor mode and transmissions from the antenna communicated from the sensor for further use in a wireless transmission mode.

2. The soil sensor of claim 1 further comprising a diplexer operatively connected to the antenna for the multiplexing.

3. The soil sensor of claim 1 wherein the antenna is a metamaterial structure.

4. The soil sensor of claim 1 further comprising a power source operatively connected to the measurement circuit and the wireless interface, the power source disposed within the housing.

5. The soil sensor of claim 1 wherein the measurement circuit is configured for periodic self-calibration using a known impedance embedded in the measurement circuit.

6. The soil sensor of claim 1 wherein the measurement circuit is configured for collecting data for determining soil moisture and the wireless interface provides for communicating the data wirelessly.

7. The soil sensor of claim 1 wherein the measurement circuit is configured for collecting data for determining electrical conductivity associated with the soil and the wireless interface provides for communicating the data wirelessly.

8. The soil sensor of claim 1 wherein the circuit is configured for collecting data for determining ion concentrations associated with the soil and the wireless interface provides for communicating the data wirelessly.

9. The soil sensor of claim 1 wherein the plurality of different frequencies are within a range of several hundred KHz to several hundred MHz.

10. The soil sensor of claim 1 wherein the one or more communication frequencies are above sensing frequency.

11. A sensor for emplacement and operation in situ at a sample comprising:
    a housing having an outside face to be exposed to the sample;
    an antenna disposed on the outside face of the housing, the antenna comprising a meta material;

a measurement circuit disposed within the housing and operatively connected to the antenna, the circuit configured to measure impedance at a plurality of different frequencies using the antenna as a sensor electrode using reflection—based spectral impedance/dielectric sensing at low RF band sensing frequencies;

a wireless interface disposed within the housing and operatively connected to the antenna and configured for wireless communications over the antenna at one or more communications frequencies, so that a parameter related to impedance of soil can be derived using a plurality of impedance measurements at the plurality of different frequencies from the antenna in a sensor mode and transmissions from the antenna communicated from the sensor for further use in a wireless transmission mode;

a power source disposed within the housing and operatively connected to the measurement circuit and the wireless interface;

wherein the measurement circuit is configured for periodic self-calibration using a known impedance embedded in the measurement circuit.

12. The sensor of claim 11 wherein the plurality of different frequencies are within a range of about a few hundred KHz to about a few hundred MHz.

13. The sensor of claim 11 wherein the one or more communication frequencies are higher than sensing frequency.

14. The sensor of claim 11 further comprising a diplexer operatively connected to the antenna.

15. A method for acquiring measurement data from a sample by emplacement and operation at the sample, the method comprising:

providing a sensor, the sensor comprising: (a) a housing having an outside face to be exposed to the sample, (b) an antenna disposed on the outside face of the housing, the antenna comprising a meta material, (c) a measurement circuit disposed within the housing and operatively connected to the antenna, the circuit configured to measure impedance at a plurality of different frequencies using the antenna as a sensor electrode using reflection—based spectral impedance/dielectric sensing at low RF band sensing frequencies, (d) a wireless interface disposed within the housing and operatively connected to the antenna and configured for wireless communications over the antenna at one or more communications frequencies, (e) a power source disposed within the housing and operatively connected to the measurement circuit and the wireless interface, wherein the measurement circuit is configured for periodic self-calibration using a known impedance embedded in the measurement circuit;

measuring impedance at a plurality of different frequencies using the antenna as a sensor electrode to provide measurement data;

wirelessly communicating the measurement data using the wireless interface and antenna for wireless transmission from the sensor.

16. The method of claim 15 further comprising determining soil moisture using the measurement data.

17. The method of claim 15 further comprising determining total ionic concentration using the measurement data.

18. The method of claim 15 further comprising performing a self calibration of the measurement circuit using the known impedance.

\* \* \* \* \*